United States Patent [19]

Sarmientos et al.

[11] Patent Number: 5,439,820

[45] Date of Patent: Aug. 8, 1995

[54] ANTI-THROMBIN POLYPEPTIDES

[75] Inventors: Paolo Sarmientos, Milan, Italy; Philippe De Taxis du Poet, Brussels, Belgium; Giampaolo Nitti, Monza; Emanuela Scacheri, Legnano, both of Italy

[73] Assignee: Farmitalia Carlo Erba S.r.l., Milan, Italy

[21] Appl. No.: 264,485

[22] Filed: Jun. 23, 1994

Related U.S. Application Data

[62] Division of Ser. No. 842,089, Feb. 26, 1992, Pat. No. 5,356,875.

[30] Foreign Application Priority Data

Feb. 28, 1991 [GB] United Kingdom ............... 9104260
Sep. 18, 1991 [GB] United Kingdom ............... 9119954

[51] Int. Cl.$^6$ ............... C12N 5/00; C12P 21/06; A61K 37/02; C07H 19/00
[52] U.S. Cl. ............... 435/240.2; 435/69.1; 435/252.3; 435/320.1; 514/2; 530/324; 536/22.1; 536/23.1; 536/23.5
[58] Field of Search ............... 435/69.1, 240.2, 252.3, 435/320.1; 514/2; 530/324; 536/22.1, 23.1, 23.5

[56] References Cited

U.S. PATENT DOCUMENTS 5,268,296  12/1993  Maschler et al. ............... 435/252.3

Primary Examiner—Robert A. Wax
Assistant Examiner—Hyosuk Kim
Attorney, Agent, or Firm—Oblon, Spivak, McClelland, Maier, & Neustadt

[57] ABSTRACT

The present invention relates to anti-thrombin polypeptides isolated from the leech *Hirudinaria manillensis* and to processes for their preparation. The polypeptides of the invention may be modified by way of amino acid extension at either or each end, and may be subjected to post-translational modification. The anti-thrombin polypeptides may be prepared by isolating them from the tissue or secretions of the leech *Hirudinaria manillensis* but they also may be synthetized by recombinant DNA methods. According to this latter aspect, the invention provides DNA sequences, expression vectors and host cell lines for the recombinant preparation of the polypeptides. The anti-thrombin polypeptides of the invention find an useful application in the treatment of venous thrombosis, vascular shunt occlusion and thrombin-induced disseminated intravascular coagulation.

18 Claims, 14 Drawing Sheets

Fig. 3.

oligo 1
5'AGCTTTGGCC AGAACTACTG CCTGTGCGTT GGTTCTAACG TTTGCGGTGA AGGTAAAAAC 3' oligo 2
5'GACAGCTGGC AGTTTTTACC TTCACCGCAA ACGTTAGAAC CAACGCACAG GCAGTAGTTC TGGCCAA 3' oligo 3
5'TGCCAGCTGT CTTCTTCTGG TAACCAGTGC GTTCACGGTG AAGGTACCCC GAAAC 3' oligo 4
5'GTCTGAGATT TCGGTTTCGG GGTACCTTCA CCGTGAACGC ACTGGTTACC AGAAGAA 3' oligo 5
5'CGAAATCTCA GACTGAAGGT GACTTCGAAG AAATTCCGGA CGAAGACATC CTGAACTAGT AACTGCA 3' oligo 6
5'GTTACTAGTT CAGGATGTCT TCGTCCGGAA TTTCTTCGAA GTCACCTTCA 3'

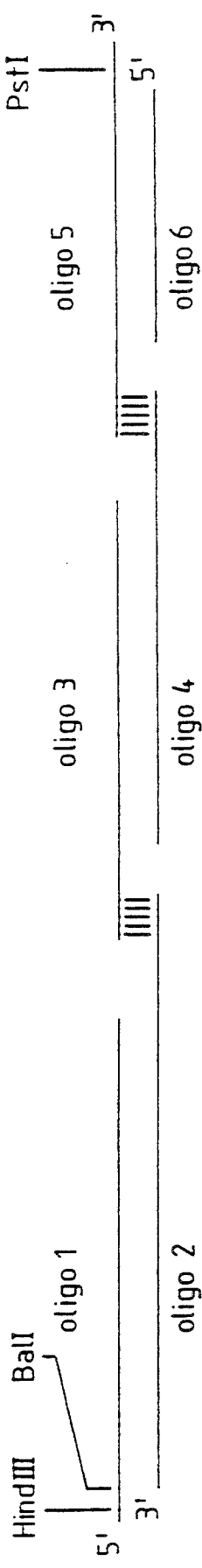

oligo 1 OmpA-P2 protein

5' AGCTTTGATA ACGAGGCGCA AAAAATGAAA AAGACAGCTA TCGCGATTGC AGTGGCACTG
GCTGGTTTCG CTACCGTAGC GCAGGCCGTT TCTTACACCG ACTGCACCGA ATCTGG 3' oligo 2 OmpA-P2 protein

5' CCAGATTCGG TGCAGTCAGT GTAAACAACG GCCTGCGCTA CGGTGGCGAA ACCAGCCAGT
GCCACTGCAA TCGCGATAGC TGTCTTTTTA GCGCCTCGTT ATCAA 3' oligo 1 fusion

5' GATCCATGGT TTCTTACACC GACTGCACCG AATCTGG 3' oligo 2 fusion

5' CCAGATTCGG TGCAGTCGGT GTAAGAAACC ATG 3'

ASSEMBLING:

Fig. 8.

oligo 1 VSV

5' AGCTTGGATC CACTATGAAG TGCCTTTTGT ACTTAGCCTT TTTATTCATT GGGGTGAATT
GCGTTTCTTA CACCGACTGC ACCGAATCTG G 3' oligo 2 VSV

5' CCAGATTCGG TGCAGTCGGT GTAAGAAACG CAATTGACCC CAATGAATAA AAAGGCTAAG
TACAAAAGGC ACTTCATAGT GGATCCA 3'

ASSEMBLING

```
      HindIII  BamHI                              BalI
         ↓      ↓                                  ↓
         ─────────────────────────────────────────
                        oligo 1
         ─────────────────────────────────────────
                        oligo 2
```

RACE: 5' END

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
        ( A ) LENGTH: 64 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( x i ) SEQUENCE DESCRIPTION: SEQ ID NO:1:

```
Val Ser Tyr Thr Asp Cys Thr Glu Ser Gly Gln Asn Tyr Cys Leu Cys
 1               5                  10                  15

Val Gly Gly Asn Leu Cys Gly Gly Gly Lys His Cys Glu Met Asp Gly
                20                  25                  30

Ser Gly Asn Lys Cys Val Asp Gly Glu Gly Thr Pro Lys Pro Lys Ser
            35                  40                  45

Gln Thr Glu Gly Asp Phe Glu Glu Ile Pro Asp Glu Asp Ile Leu Asn
        50                  55                  60
```

( 2 ) INFORMATION FOR SEQ ID NO:2:

( i ) SEQUENCE CHARACTERISTICS:
        ( A ) LENGTH: 64 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( x i ) SEQUENCE DESCRIPTION: SEQ ID NO:2:

```
Val Ser Tyr Thr Asp Cys Thr Glu Ser Gly Gln Asn Tyr Cys Leu Cys
 1               5                  10                  15
```

Val Gly Ser Asn Val Cys Gly Glu Gly Lys Asn Cys Gln Leu Ser Ser
            20                      25                      30

Ser Gly Asn Gln Cys Val His Gly Glu Gly Thr Pro Lys Pro Lys Ser
            35                      40                      45

Gln Thr Glu Gly Asp Phe Glu Ile Pro Asp Glu Asp Ile Leu Asn
    50                      55                      60

(2) INFORMATION FOR SEQ ID NO:3:

(i) SEQUENCE CHARACTERISTICS:
  (A) LENGTH: 42 amino acids
  (B) TYPE: amino acid
  (D) TOPOLOGY: linear (ii) MOLECULE TYPE: peptide (vi) ORIGINAL SOURCE:
  (A) ORGANISM: Hirudinaria manillensis (xi) SEQUENCE DESCRIPTION: SEQ ID NO:3:

Val Ser Tyr Thr Asp Cys Thr Glu Ser Gly Gln Asn Tyr Cys Leu Cys
1               5                       10                      15

Val Gly Ser Asn Val Cys Gly Glu Gly Lys Asn Cys Gln Leu Ser Ser
            20                      25                      30

Ser Gly Asn Gln Cys Val His Gly Glu Gly
            35                      40

(2) INFORMATION FOR SEQ ID NO:4:

(i) SEQUENCE CHARACTERISTICS:
  (A) LENGTH: 20 amino acids
  (B) TYPE: amino acid
  (D) TOPOLOGY: linear (ii) MOLECULE TYPE: peptide (vi) ORIGINAL SOURCE:
  (A) ORGANISM: Hirudinaria manillensis (xi) SEQUENCE DESCRIPTION: SEQ ID NO:4:

Met Phe Ser Leu Lys Leu Phe Val Val Phe Leu Ala Val Cys Ile Cys
1               5                       10                      15

Val Ser Gln Ala
            20

(2) INFORMATION FOR SEQ ID NO:5:

(i) SEQUENCE CHARACTERISTICS:
  (A) LENGTH: 63 base pairs
  (B) TYPE: nucleic acid
  (C) STRANDEDNESS: double
  (D) TOPOLOGY: linear (ii) MOLECULE TYPE: DNA (genomic)

(vi) ORIGINAL SOURCE:
  (A) ORGANISM: Escherichia coli (ix) FEATURE:
  (A) NAME/KEY: miscfeature
  (B) LOCATION: 1..63
  (D) OTHER INFORMATION: /function="leader peptide"
   /standardname="OmpA leader"

(xi) SEQUENCE DESCRIPTION: SEQ ID NO:5:

ATGAAAAAGA CAGCTATCGC GATTGCAGTG GCACTGGCTG GTTTCGCTAC CGTAGCGCAG   60

GCC   63

(2) INFORMATION FOR SEQ ID NO:6:

( i ) SEQUENCE CHARACTERISTICS:
    ( A ) LENGTH: 48 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: vesicular stomatitis virus ( i x ) FEATURE:
    ( A ) NAME/KEY: miscfeature
( B ) LOCATION: 1..48
( D ) OTHER INFORMATION: /function="leader peptide"
/ standardname="VSV G leader"

( x i ) SEQUENCE DESCRIPTION: SEQ ID NO:6:

ATGAAGTGCC TTTTGTACTT AGCCTTTTTA TTCATTGGGG TGAATTGC 48

( 2 ) INFORMATION FOR SEQ ID NO:7:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Hirudinaria manillensis ( v i i ) IMMEDIATE SOURCE:
( B ) CLONE: oligo 1

( x i ) SEQUENCE DESCRIPTION: SEQ ID NO:7:

AGCTTTGGCC AGAACTACTG CCTGTGCGTT GGTTCTAACG TTTGCGGTGA AGGTAAAAAC 60

( 2 ) INFORMATION FOR SEQ ID NO:8:

( i ) SEQUENCE CHARACTERISTICS:
( A ) LENGTH: 67 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Hirudinaria manillensis ( v i i ) IMMEDIATE SOURCE:
( B ) CLONE: oligo 2

( x i ) SEQUENCE DESCRIPTION: SEQ ID NO:8:

GACAGCTGGC AGTTTTTACC TTCACCGCAA ACGTTAGAAC CAACGCACAG GCAGTAGTTC 60

TGGCCAA 67

( 2 ) INFORMATION FOR SEQ ID NO:9:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Hirudinaria manillensis ( v i i ) IMMEDIATE SOURCE:
( B ) CLONE: oligo 3

( x i ) SEQUENCE DESCRIPTION: SEQ ID NO:9:

TGCCAGCTGT CTTCTTCTGG TAACCAGTGC GTTCACGGTG AAGGTACCCC GAAAC  55

( 2 ) INFORMATION FOR SEQ ID NO:10:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Hirudinaria manillensis ( v i i ) IMMEDIATE SOURCE:
        ( B ) CLONE: oligo 4

( x i ) SEQUENCE DESCRIPTION: SEQ ID NO:10:

GTCTGAGATT TCGGTTTCGG GGTACCTTCA CCGTGAACGC ACTGGTTACC AGAAGAA  57

( 2 ) INFORMATION FOR SEQ ID NO:11:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Hirudinaria manillensis ( v i i ) IMMEDIATE SOURCE:
        ( B ) CLONE: oligo 5

( x i ) SEQUENCE DESCRIPTION: SEQ ID NO:11:

CGAAATCTCA GACTGAAGGT GACTTCGAAG AAATTCCGGA CGAAGACATC CTGAACTAGT  60

AACTGCA  67

( 2 ) INFORMATION FOR SEQ ID NO:12:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Hirudinaria manillensis ( v i i ) IMMEDIATE SOURCE:
        ( B ) CLONE: oligo 6

( x i ) SEQUENCE DESCRIPTION: SEQ ID NO:12:

GTTACTAGTT CAGGATGTCT TCGTCCGGAA TTTCTTCGAA GTCACCTTCA  50

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( i x ) FEATURE:
    ( A ) NAME/KEY: Region
    ( B ) LOCATION: 1..13
    ( D ) OTHER INFORMATION: /note="This sequence corresponds to amino acids 1-13 of SEQ ID NO:1."

( x i ) SEQUENCE DESCRIPTION: SEQ ID NO:13:

Val Ser Tyr Thr Asp Cys Thr Glu Ser Gly Gln Asn Tyr
1               5                   10

( 2 ) INFORMATION FOR SEQ ID NO:14:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( i x ) FEATURE:
        ( A ) NAME/KEY: Region
        ( B ) LOCATION: 1..13
        ( D ) OTHER INFORMATION: /note="This sequence corresponds to amino acids 14-26 of SEQ ID NO:1."

( x i ) SEQUENCE DESCRIPTION: SEQ ID NO:14:

Cys Leu Cys Val Gly Gly Asn Leu Cys Gly Gly Gly Lys
1               5                   10

( 2 ) INFORMATION FOR SEQ ID NO:15:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( i x ) FEATURE:
        ( A ) NAME/KEY: Region
        ( B ) LOCATION: 1..10
        ( D ) OTHER INFORMATION: /note="This sequence corresponds to amino acids 27-36 of SEQ ID NO:1."

( x i ) SEQUENCE DESCRIPTION: SEQ ID NO:15:

His Cys Glu Met Asp Gly Ser Gly Asn Lys
1               5                   10

( 2 ) INFORMATION FOR SEQ ID NO:16:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( i x ) FEATURE:
        ( A ) NAME/KEY: Region
        ( B ) LOCATION: 1..11
        ( D ) OTHER INFORMATION: /note="This sequence corresponds to amino acids 37-47 of SEQ ID NO:1."

( x i ) SEQUENCE DESCRIPTION: SEQ ID NO:16:

Cys Val Asp Gly Glu Gly Thr Pro Lys Pro Lys ( 2 ) INFORMATION FOR SEQ ID NO:17:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( i x ) FEATURE:
        ( A ) NAME/KEY: Region
        ( B ) LOCATION: 1..11
        ( D ) OTHER INFORMATION: /note="This sequence corresponds
            to amino acids 37-47 of SEQ ID NO:1."

( x i ) SEQUENCE DESCRIPTION: SEQ ID NO:17:

```
Cys  Val  Asp  Gly  Glu  Gly  Xaa  Pro  Lys  Pro  Lys
 1                  5                        10
```

( 2 ) INFORMATION FOR SEQ ID NO:18:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( i x ) FEATURE:
        ( A ) NAME/KEY: Region
        ( B ) LOCATION: 1..16
        ( D ) OTHER INFORMATION: /note="This sequence corresponds
            to amino acids 48-64 of SEQ ID NO:1."

( x i ) SEQUENCE DESCRIPTION: SEQ ID NO:18:

```
Ser  Gln  Thr  Glu  Gly  Asp  Phe  Glu  Glu  Ile  Pro  Asp  Glu  Asp  Ile  Leu
 1                  5                        10                       15
Asn
```

( 2 ) INFORMATION FOR SEQ ID NO:19:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( i x ) FEATURE:
        ( A ) NAME/KEY: Region
        ( B ) LOCATION: 1..13
        ( D ) OTHER INFORMATION: /note="This sequence corresponds
            to amino acids 1-13 of SEQ ID NO:1."

( x i ) SEQUENCE DESCRIPTION: SEQ ID NO:19:

```
Val  Ser  Tyr  Thr  Asp  Cys  Thr  Glu  Ser  Gly  Gln  Asn  Tyr
 1                  5                        10
```

( 2 ) INFORMATION FOR SEQ ID NO:20:

( i ) SEQUENCE CHARACTERISTICS:
        ( A ) LENGTH: 13 amino acids
        ( B ) TYPE: amino acid (D) TOPOLOGY: linear (ii) MOLECULE TYPE: peptide (vi) ORIGINAL SOURCE:
    (A) ORGANISM: Hirudinaria manillensis (ix) FEATURE:
    (A) NAME/KEY: Region
    (B) LOCATION: 1..13
    (D) OTHER INFORMATION: /note="This sequence corresponds
        to amino acids 14-26 of SEQ ID NO:1."

(xi) SEQUENCE DESCRIPTION: SEQ ID NO:20:

```
Cys  Leu  Cys  Val  Gly  Ser  Asn  Val  Cys  Gly  Glu  Gly  Lys
 1              5                        10
```

(2) INFORMATION FOR SEQ ID NO:21:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (vi) ORIGINAL SOURCE:
        (A) ORGANISM: Hirudinaria manillensis (ix) FEATURE:
        (A) NAME/KEY: Region
        (B) LOCATION: 1..21
        (D) OTHER INFORMATION: /note="This sequence corresponds
            to amino acids 26-47 of SEQ ID NO:1."

(xi) SEQUENCE DESCRIPTION: SEQ ID NO:21:

```
Asn  Cys  Gln  Leu  Ser  Ser  Ser  Gly  Asn  Gln  Cys  Val  His  Gly  Glu  Gly
 1              5                        10                       15

Xaa  Pro  Lys  Pro  Lys
              20
```

(2) INFORMATION FOR SEQ ID NO:22:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (vi) ORIGINAL SOURCE:
        (A) ORGANISM: Hirudinaria manillensis (ix) FEATURE:
        (A) NAME/KEY: Region
        (B) LOCATION: 1..17
        (D) OTHER INFORMATION: /note="This sequence corresponds
            to amino acids 48-64 of SEQ ID NO:2."

(xi) SEQUENCE DESCRIPTION: SEQ ID NO:22:

```
Ser  Gln  Thr  Glu  Gly  Asp  Phe  Glu  Glu  Ile  Pro  Asp  Glu  Asp  Ile  Leu
 1              5                        10                       15

Asn
```

(2) INFORMATION FOR SEQ ID NO:23:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (genomic)

-continued ( v i ) ORIGINAL SOURCE:
( A ) ORGANISM: Escherichia coli and Hirudinaria manillensis ( v i i ) IMMEDIATE SOURCE:
( B ) CLONE: oligo 1 OmpA-P2 protein ( x i ) SEQUENCE DESCRIPTION: SEQ ID NO:23:

AGCTTTGATA ACGAGGCGCA AAAAATGAAA AAGACAGCTA TCGCGATTGC AGTGGCACTG 60

GCTGGTTTCG CTACCGTAGC GCAGGCCGTT TCTTACACCG ACTGCACCGA ATCTGG 116

( 2 ) INFORMATION FOR SEQ ID NO:24:

( i ) SEQUENCE CHARACTERISTICS:
( A ) LENGTH: 105 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Escherichia coli and Hirudinaria manillensis ( v i i ) IMMEDIATE SOURCE:
( B ) CLONE: oligo 2 OmpA-P2 protein ( x i ) SEQUENCE DESCRIPTION: SEQ ID NO:24:

CCAGATTCGG TGCAGTCAGT GTAAACAACG GCCTGCGCTA CGGTGGCGAA ACCAGCCAGT 60

GCCACTGCAA TCGCGATAGC TGTCTTTTTA GCGCCTCGTT ATCAA 105

( 2 ) INFORMATION FOR SEQ ID NO:25:

( i ) SEQUENCE CHARACTERISTICS:
( A ) LENGTH: 91 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: vesicular stomatitis virus ( v i i ) IMMEDIATE SOURCE:
( B ) CLONE: oligo 1 VSV ( x i ) SEQUENCE DESCRIPTION: SEQ ID NO:25:

AGCTTGGATC CACTATGAAG TGCCTTTTGT ACTTAGCCTT TTTATTCATT GGGGTGAATT 60

GCGTTTCTTA CACCGACTGC ACCGAATCTG G 91

( 2 ) INFORMATION FOR SEQ ID NO:26:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: vesicular stomatitis virus ( v i i ) IMMEDIATE SOURCE:
( B ) CLONE: oligo 2 VSV ( x i ) SEQUENCE DESCRIPTION: SEQ ID NO:26:

CCAGATTCGG TGCAGTCGGT GTAAGAAACG CAATTGACCC CAATGAATAA AAAGGCTAAG 60

TACAAAAGGC ACTTCATAGT GGATCCA 87

( 2 ) INFORMATION FOR SEQ ID NO:27:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Hirudinaria manillensis ( v i i ) IMMEDIATE SOURCE:
        ( B ) CLONE: oligo 1 fusion ( x i ) SEQUENCE DESCRIPTION: SEQ ID NO:27:

GATCCATGGT TTCTTACACC GACTGCACCG AATCTGG                                                   37

( 2 ) INFORMATION FOR SEQ ID NO:28:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Hirudinaria manillensis ( v i i ) IMMEDIATE SOURCE:
        ( B ) CLONE: oligo 2 fusion ( x i ) SEQUENCE DESCRIPTION: SEQ ID NO:28:

CCAGATTCGG TGCAGTCGGT GTAAGAAACC ATG                                                           33

( 2 ) INFORMATION FOR SEQ ID NO:29:

( i ) SEQUENCE CHARACTERISTICS:
        ( A ) LENGTH: 150 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: baculovirus ( v i i ) IMMEDIATE SOURCE:
        ( B ) CLONE: oligo 1 polyhedrin ( x i ) SEQUENCE DESCRIPTION: SEQ ID NO:29:

ATCATGGAGA TAATTAAAAT GATAACCATC TCGCAAATAA ATAAGTATTT TACTGTTTTC      60

GTAACAGTTT TGTAATAAAA AAACCTATAA ATATGCCGGA TTATTCATAC CGTCCCACCA     120

TCGGGCGTAC CTACGTGTAC GACAACACCG                                                         150

( 2 ) INFORMATION FOR SEQ ID NO:30:

( i ) SEQUENCE CHARACTERISTICS:
        ( A ) LENGTH: 154 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: baculovirus ( v i i ) IMMEDIATE SOURCE:
        ( B ) CLONE: oligo 2 polyhedrin ( x i ) SEQUENCE DESCRIPTION: SEQ ID NO:30:

GATCCGGTGT TGTCGTACAC GTAGGTACGC CCGATGGTGG GACGGTATGA ATAATCCGGC    60

ATATTTATAG GTTTTTTAT TACAAAACTG TTACGAAAAC AGTAGAATAC TTATTTATTT    120

GCGAGATGGT TATCATTTTA ATTATCTCCA TGAT    154

( 2 ) INFORMATION FOR SEQ ID NO:31:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Hirudinaria manillensis ( i x ) FEATURE:
        ( A ) NAME/KEY: miscfeature
        ( B ) LOCATION: 45..47
        ( D ) OTHER INFORMATION: /note="The TAC codon replaces GAC
            to obtain the Tyr-61 variant of P2."

( x i ) SEQUENCE DESCRIPTION: SEQ ID NO:31:

CGAAATCTCA GACTGAAGGT GACTTCGAAG AAATTCCGGA CGAATACATC CTGAACTAGT    60

AACTGCA    67

( 2 ) INFORMATION FOR SEQ ID NO:32:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Hirudinaria manillensis ( i x ) FEATURE:
        ( A ) NAME/KEY: miscfeature
        ( B ) LOCATION: 17..19
        ( D ) OTHER INFORMATION: /note="GTA replaces GTC to obtain
            complete complementarity to SEQ ID NO:18."

( x i ) SEQUENCE DESCRIPTION: SEQ ID NO:32:

GTTACTAGTT CAGGATGTAT TCGTCCGGAA TTTCTTCGAA GTCACCTTCA    50

( 2 ) INFORMATION FOR SEQ ID NO:33:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Hirudinaria manillensis ( i x ) FEATURE:
        ( A ) NAME/KEY: miscfeature
        ( B ) LOCATION: 58..60
        ( D ) OTHER INFORMATION: /note="GGT is inserted before the
            stop codon."

( x i ) SEQUENCE DESCRIPTION: SEQ ID NO:33:

CGAAATCTCA GACTGAAGGT GACTTCGAAG AAATTCCGGA CGAAGACATC CTGAACGGTT    60

AGTAACTGCA 70

(2) INFORMATION FOR SEQ ID NO:34:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Hirudinaria manillensis (ix) FEATURE:
        (A) NAME/KEY: miscfeature
        (B) LOCATION: 7..9
        (D) OTHER INFORMATION: /note="ACC inserted to obtain
            complete complementarity to SEQ ID NO:20."

(xi) SEQUENCE DESCRIPTION: SEQ ID NO:34:

GTTACTAACC GTTCAGGATG TCTTCGTCCG GAATTCTTC GAAGTCACCT TCA 53

(2) INFORMATION FOR SEQ ID NO:35:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GACTCGAGTC GACATCGATT TTTTTTTTT TTTTT 35

(2) INFORMATION FOR SEQ ID NO:36:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

GACTCGAGTC GACATCG 17

(2) INFORMATION FOR SEQ ID NO:37:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

ATCGAAGCTT TATACCGATT GTACNGA 27

(2) INFORMATION FOR SEQ ID NO:38:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

( x i ) SEQUENCE DESCRIPTION: SEQ ID NO:38:

CTAAGGATCC TTCTTCGAAG TCNCC  25

( 2 ) INFORMATION FOR SEQ ID NO:39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

ATCGGAATTC AGTTCTGGAA ATCAGTGCGT  30

( 2 ) INFORMATION FOR SEQ ID NO:40:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

CTAAGAATTC TTCGCAACTT ATATGCGTT  29

( 2 ) INFORMATION FOR SEQ ID NO:41:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

ATCGGAATTC TTAATTCAAT ATATCTTCAT  30

( 2 ) INFORMATION FOR SEQ ID NO:42:

( i ) SEQUENCE CHARACTERISTICS:
        ( A ) LENGTH: 258 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Hirudinaria manillensis ( v i i ) IMMEDIATE SOURCE:
        ( B ) CLONE: P1 cDNA ( x i ) SEQUENCE DESCRIPTION: SEQ ID NO:42:

TCAAAAATGT TCTCTCTCAA GTTGTTCGTT GTCTTCCTGG CTGTTTGCAT CTGCGTGTCT  60
CAAGCAGTGA GCTACACTGA TTGTACGGAA TCAGGCCAGA ATTATTGTCT ATGCGTGGGA  120
GGTAATCTCT GCGGTGGCAA ACATTGTGAA ATGGACGGTT CTGGAAATAA ATGCGTCGAT  180
GGGGAAGGTA CTCCGAAGCC TAAGAGCCAG ACTGAAGGCG ATTTCGAAGA AATCCCAGAT  240
GAAGATATAT TGAATTAA  258

( 2 ) INFORMATION FOR SEQ ID NO:43:

( i ) SEQUENCE CHARACTERISTICS:
    ( A ) LENGTH: 84 amino acids
    ( B ) TYPE: amino acid
    ( D ) TOPOLOGY: linear ( i i ) MOLECULE TYPE: protein ( x i ) SEQUENCE DESCRIPTION: SEQ ID NO:43:

```
Met Phe Ser Leu Lys Leu Phe Val Val Phe Leu Ala Val Cys Ile Cys
 1               5                  10                  15

Val Ser Gln Ala Val Ser Tyr Thr Asp Cys Thr Glu Ser Gly Gln Asn
                20                  25                  30

Tyr Cys Leu Cys Val Gly Gly Asn Leu Cys Gly Gly Gly Lys His Cys
            35                  40                  45

Glu Met Asp Gly Ser Gly Asn Lys Cys Val Asp Gly Glu Gly Thr Pro
        50                  55                  60

Lys Pro Lys Ser Gln Thr Glu Gly Asp Phe Glu Glu Ile Pro Asp Glu
65                  70                  75                  80

Asp Ile Leu Asn
```

( 2 ) INFORMATION FOR SEQ ID NO:44:

( i ) SEQUENCE CHARACTERISTICS:
        ( A ) LENGTH: 369 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Hirudinaria manillensis ( v i i ) IMMEDIATE SOURCE:
        ( B ) CLONE: P2 cDNA ( x i ) SEQUENCE DESCRIPTION: SEQ ID NO:44:

```
AAAATGTTCT CTCTCAAGTT GTTCGTTGTC TTCCTGGCTG TTTGCATCTG CGTGTCTCAA      60
GCAGTGAGCT ACACTGATTG TACGGAATCA GGTCAGAATT ATTGTCTATG CGTGGGAAGT     120
AATGTCTGCG GTGGAGGCAA AAATTGTCAA CTGAGCAGTT CTGGAAATCA GTGCGTCCAT     180
GGGGAAGGTA CTCCGAAGCC TAAGAGCCAG ACTGAAGGCG ATTTCGAAGA AATCCCAGAT     240
GAAGATATAT TGAATTAACG AACGCATATA AGTTGCGAAT AATTCTGATT TTAAGACATT     300
CCCATCGCAG CTATGGCTAT TTACAGTATA TTATTATAAA TAAAGAATTG AACGTTTACG     360
TTGATTGTA                                                             369
```

( 2 ) INFORMATION FOR SEQ ID NO:45:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

```
Met Phe Ser Leu Lys Leu Phe Val Val Phe Leu Ala Val Cys Ile Cys
 1               5                  10                  15

Val Ser Gln Ala Val Ser Tyr Thr Asp Cys Thr Glu Ser Gly Gln Asn
                20                  25                  30

Tyr Cys Leu Cys Val Gly Ser Asn Val Cys Gly Glu Gly Lys Asn Cys
            35                  40                  45

Gln Leu Ser Ser Ser Gly Asn Gln Cys Val His Gly Glu Gly Thr Pro
        50                  55                  60
```

```
Lys  Pro  Lys  Ser  Gln  Thr  Glu  Gly  Asp  Phe  Glu  Glu  Ile  Pro  Asp  Glu
 65                  70                       75                      80

Asp  Ile  Leu  Asn
```

( 2 ) INFORMATION FOR SEQ ID NO:46:

( i ) SEQUENCE CHARACTERISTICS:
        ( A ) LENGTH: 195 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Hirudinaria manillensis ( i x ) FEATURE:
        ( A ) NAME/KEY: miscfeature
        ( B ) LOCATION: 1..195
        ( D ) OTHER INFORMATION: /product="alternate sequence encoding P2"

( x i ) SEQUENCE DESCRIPTION: SEQ ID NO:46:

```
GTTTCTTACA  CCGACTGCAC  CGAATCTGGC  CAGAACTACT  GCCTGTGCGT  TGGTTCTAAC      60

GTTTGCGGTG  AAGGTAAAAA  CTGCCAGCTG  TCTTCTTCTG  GTAACCAGTG  CGTTCACGGT     120

GAAGGTACCC  CGAAACCGAA  ATCTCAGACT  GAAGGTGACT  TCGAAGAAAT  TCCGGACGAA     180

GACATCCTGA  ACTAG                                                         195
```

( 2 ) INFORMATION FOR SEQ ID NO:47:

( i ) SEQUENCE CHARACTERISTICS:
        ( A ) LENGTH: 195 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Hirudinaria manillensis ( i x ) FEATURE:
        ( A ) NAME/KEY: miscfeature
        ( B ) LOCATION: 1..195
        ( D ) OTHER INFORMATION: /product="encodes amino acid 21 (Val) through stop codon of P1"

( x i ) SEQUENCE DESCRIPTION: SEQ ID NO:47:

```
GTGAGCTACA  CTGATTGTAC  GGAATCAGGC  CAGAATTATT  GTCTATGCGT  GGGAGGTAAT      60

CTCTGCGGTG  GAGGCAAACA  TTGTGAAATG  GACGGTTCTG  GAAATAAATG  CGTCGATGGG     120

GAAGGTACTC  CGAAGCCTAA  GAGCCAGACT  GAAGGCGATT  TCGAAGAAAT  CCCAGATGAA     180

GATATATTGA  ATTAA                                                         195
```

( 2 ) INFORMATION FOR SEQ ID NO:48:

( i ) SEQUENCE CHARACTERISTICS:
        ( A ) LENGTH: 255 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Hirudinaria manillensis ( x i ) SEQUENCE DESCRIPTION: SEQ ID NO:48:

```
ATGTTCTCTC TCAAGTTGTT CGTTGTCTTC CTGGCTGTTT GCATCTGCGT GTCTCAAGCA      60

GTGAGCTACA CTGATTGTAC GGAATCAGGT CAGAATTATT GTCTATGCGT GGGAAGTAAT     120

CTCTGCGGTG GAGGCAAAAA TTGTCAACTG AGCAGTTCTG GAAATCAGTG CGTCCATGGG     180

GAAGGTACTC CGAAGCCTAA GAGCCAGACT GAAGGCGATT TCGAAGAAAT CCCAGATGAA     240

GATATATTGA ATTAA                                                      255
```

(2) INFORMATION FOR SEQ ID NO:49:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Hirudinaria manillensis (ix) FEATURE:
        (A) NAME/KEY: miscfeature
        (B) LOCATION: 1..60
        (D) OTHER INFORMATION: /product="leader sequence for P1 and P (xi) SEQUENCE DESCRIPTION: SEQ ID NO:49:

```
ATGTTCTCTC TCAAGTTGTT CGTTGTCTTC CTGGCTGTTT GCATCTGCGT GTCTCAAGCA      60
```

(2) INFORMATION FOR SEQ ID NO:50:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (vi) ORIGINAL SOURCE:
        (A) ORGANISM: Hirudinaria manillensis (xi) SEQUENCE DESCRIPTION: SEQ ID NO:50:

```
Val Ser Tyr Thr Asp Cys Thr Glu Ser Gly Gln Asn Tyr Cys Leu Cys
 1               5                  10                  15

Val Gly Gly Asn Leu Cys Gly Gly Lys His Cys Glu Met Asp Gly
            20                  25                  30

Ser Gly Asn Lys Cys Val Asp Gly Glu Gly Thr Pro Lys Pro Lys Ser
            35                  40                  45

Gln Thr Glu Gly Asp Phe Glu Glu Ile Pro Asp Glu Asp Ile Leu Asn
        50                  55                  60

Gly

65
```

(2) INFORMATION FOR SEQ ID NO:51:

(i) SEQUENCE CHARACTERISTICS:
        (A) LENGTH: 64 amino acids
        (B) TYPE: amino acid
        (D) TOPOLOGY: linear (ii) MOLECULE TYPE: peptide (vi) ORIGINAL SOURCE:
        (A) ORGANISM: Hirudinaria manillensis (ix) FEATURE:
        (A) NAME/KEY: Modified-site
        (B) LOCATION: 64
        (D) OTHER INFORMATION: /note="Asn-64 contains a terminal
            amide group."

( x i ) SEQUENCE DESCRIPTION: SEQ ID NO:51:

| Val | Ser | Tyr | Thr | Asp | Cys | Thr | Glu | Ser | Gly | Gln | Asn | Tyr | Cys | Leu | Cys |
|---|---|---|---|---|---|---|---|---|---|---|---|---|---|---|---|
| 1 | | | | 5 | | | | | 10 | | | | | 15 | |

| Val | Gly | Gly | Asn | Leu | Cys | Gly | Gly | Gly | Lys | His | Cys | Glu | Met | Asp | Gly |
|---|---|---|---|---|---|---|---|---|---|---|---|---|---|---|---|
| | | | 20 | | | | | 25 | | | | | 30 | | |

| Ser | Gly | Asn | Lys | Cys | Val | Asp | Gly | Glu | Gly | Thr | Pro | Lys | Pro | Lys | Ser |
|---|---|---|---|---|---|---|---|---|---|---|---|---|---|---|---|
| | | 35 | | | | | 40 | | | | | 45 | | | |

| Gln | Thr | Glu | Gly | Asp | Phe | Glu | Glu | Ile | Pro | Asp | Glu | Asp | Ile | Leu | Asn |
|---|---|---|---|---|---|---|---|---|---|---|---|---|---|---|---|
| | 50 | | | | | 55 | | | | | 60 | | | | |

( 2 ) INFORMATION FOR SEQ ID NO:52:

( i ) SEQUENCE CHARACTERISTICS:
        ( A ) LENGTH: 64 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( x i ) SEQUENCE DESCRIPTION: SEQ ID NO:52:

| Val | Ser | Tyr | Thr | Asp | Cys | Thr | Glu | Ser | Gly | Gln | Asn | Tyr | Cys | Leu | Cys |
|---|---|---|---|---|---|---|---|---|---|---|---|---|---|---|---|
| 1 | | | | 5 | | | | | 10 | | | | | 15 | |

| Val | Gly | Gly | Asn | Leu | Cys | Gly | Gly | Gly | Lys | His | Cys | Glu | Met | Asp | Gly |
|---|---|---|---|---|---|---|---|---|---|---|---|---|---|---|---|
| | | | 20 | | | | | 25 | | | | | 30 | | |

| Ser | Gly | Asn | Lys | Cys | Val | Asp | Gly | Glu | Gly | Thr | Pro | Lys | Pro | Lys | Ser |
|---|---|---|---|---|---|---|---|---|---|---|---|---|---|---|---|
| | | 35 | | | | | 40 | | | | | 45 | | | |

| Gln | Thr | Glu | Gly | Asp | Phe | Glu | Glu | Ile | Pro | Asp | Glu | Tyr | Ile | Leu | Asn |
|---|---|---|---|---|---|---|---|---|---|---|---|---|---|---|---|
| | 50 | | | | | 55 | | | | | 60 | | | | |

( 2 ) INFORMATION FOR SEQ ID NO:53:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( x i ) SEQUENCE DESCRIPTION: SEQ ID NO:53:

| Val | Ser | Tyr | Thr | Asp | Cys | Thr | Glu | Ser | Gly | Gln | Asn | Tyr | Cys | Leu | Cys |
|---|---|---|---|---|---|---|---|---|---|---|---|---|---|---|---|
| 1 | | | | 5 | | | | | 10 | | | | | 15 | |

| Val | Gly | Gly | Asn | Leu | Cys | Gly | Gly | Gly | Lys | His | Cys | Glu | Met | Asp | Gly |
|---|---|---|---|---|---|---|---|---|---|---|---|---|---|---|---|
| | | | 20 | | | | | 25 | | | | | 30 | | |

| Ser | Gly | Asn | Lys | Cys | Val | Asp | Gly | Glu | Gly | Thr | Pro | Lys | Pro | Lys | Ser |
|---|---|---|---|---|---|---|---|---|---|---|---|---|---|---|---|
| | | 35 | | | | | 40 | | | | | 45 | | | |

| Gln | Thr | Glu | Gly | Asp | Phe | Glu | Glu | Ile | Pro | Asp | Glu | Tyr | Ile | Leu | Asn |
|---|---|---|---|---|---|---|---|---|---|---|---|---|---|---|---|
| | 50 | | | | | 55 | | | | | 60 | | | | |

| Gly |
|---|
| 65 |

( 2 ) INFORMATION FOR SEQ ID NO:54:

( i ) SEQUENCE CHARACTERISTICS:
        ( A ) LENGTH: 64 amino acids
        ( B ) TYPE: amino acid
        ( D ) TOPOLOGY: linear ( i i ) MOLECULE TYPE: peptide ( v i ) ORIGINAL SOURCE:
    ( A ) ORGANISM: Hirudinaria manillensis ( i x ) FEATURE:
    ( A ) NAME/KEY: Modified-site
    ( B ) LOCATION: 64
    ( D ) OTHER INFORMATION: /note="Asn-64 contains a terminal
        amide group."

( x i ) SEQUENCE DESCRIPTION: SEQ ID NO:54:

```
Val Ser Tyr Thr Asp Cys Thr Glu Ser Gly Gln Asn Tyr Cys Leu Cys
 1               5                  10                  15

Val Gly Gly Asn Leu Cys Gly Gly Gly Lys His Cys Glu Met Asp Gly
             20                  25                  30

Ser Gly Asn Lys Cys Val Asp Gly Glu Gly Thr Pro Lys Pro Lys Ser
             35                  40                  45

Gln Thr Glu Gly Asp Phe Glu Glu Ile Pro Asp Glu Tyr Ile Leu Asn
     50                  55                  60
```

( 2 ) INFORMATION FOR SEQ ID NO:55:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( x i ) SEQUENCE DESCRIPTION: SEQ ID NO:55:

```
Val Ser Tyr Thr Asp Cys Thr Glu Ser Gly Gln Asn Tyr Cys Leu Cys
 1               5                  10                  15

Val Gly Ser Asn Val Cys Gly Glu Gly Lys Asn Cys Gln Leu Ser Ser
             20                  25                  30

Ser Gly Asn Gln Cys Val His Gly Glu Gly Thr Pro Lys Pro Lys Ser
             35                  40                  45

Gln Thr Glu Gly Asp Phe Glu Glu Ile Pro Asp Glu Asp Ile Leu Asn
     50                  55                  60

Gly
 6 5
```

( 2 ) INFORMATION FOR SEQ ID NO:56:

( i ) SEQUENCE CHARACTERISTICS:
        ( A ) LENGTH: 64 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Hirudinaria manillensis ( i x ) FEATURE:
        ( A ) NAME/KEY: Modified-site
        ( B ) LOCATION: 64
        ( D ) OTHER INFORMATION: /note="Asn-64 contains a terminal
            amide group."

( x i ) SEQUENCE DESCRIPTION: SEQ ID NO:56:

```
Val Ser Tyr Thr Asp Cys Thr Glu Ser Gly Gln Asn Tyr Cys Leu Cys
 1               5                  10                  15

Val Gly Ser Asn Val Cys Gly Glu Gly Lys Asn Cys Gln Leu Ser Ser
             20                  25                  30
```

```
        Ser  Gly  Asn  Gln  Cys  Val  His  Gly  Glu  Gly  Thr  Pro  Lys  Pro  Lys  Ser
                  35                       40                      45

Gln  Thr  Glu  Gly  Asp  Phe  Glu  Glu  Ile  Pro  Asp  Glu  Asp  Ile  Leu  Asn
             50                       55                      60
```

(2) INFORMATION FOR SEQ ID NO:57:

(i) SEQUENCE CHARACTERISTICS:
        (A) LENGTH: 64 amino acids
        (B) TYPE: amino acid
        (D) TOPOLOGY: linear (ii) MOLECULE TYPE: peptide (vi) ORIGINAL SOURCE:
        (A) ORGANISM: Hirudinaria manillensis (xi) SEQUENCE DESCRIPTION: SEQ ID NO:57:

```
        Val  Ser  Tyr  Thr  Asp  Cys  Thr  Glu  Ser  Gly  Gln  Asn  Tyr  Cys  Leu  Cys
        1                   5                        10                       15

Val  Gly  Ser  Asn  Val  Cys  Gly  Glu  Gly  Lys  Asn  Cys  Gln  Leu  Ser  Ser
                  20                       25                      30

Ser  Gly  Asn  Gln  Cys  Val  His  Gly  Glu  Gly  Thr  Pro  Lys  Pro  Lys  Ser
                  35                       40                      45

Gln  Thr  Glu  Gly  Asp  Phe  Glu  Glu  Ile  Pro  Asp  Glu  Tyr  Ile  Leu  Asn
             50                       55                      60
```

(2) INFORMATION FOR SEQ ID NO:58:

(i) SEQUENCE CHARACTERISTICS:
        (A) LENGTH: 65 amino acids
        (B) TYPE: amino acid
        (D) TOPOLOGY: linear (ii) MOLECULE TYPE: peptide (vi) ORIGINAL SOURCE:
        (A) ORGANISM: Hirudinaria manillensis (xi) SEQUENCE DESCRIPTION: SEQ ID NO:58:

```
        Val  Ser  Tyr  Thr  Asp  Cys  Thr  Glu  Ser  Gly  Gln  Asn  Tyr  Cys  Leu  Cys
        1                   5                        10                       15

Val  Gly  Ser  Asn  Val  Cys  Gly  Glu  Gly  Lys  Asn  Cys  Gln  Leu  Ser  Ser
                  20                       25                      30

Ser  Gly  Asn  Gln  Cys  Val  His  Gly  Glu  Gly  Thr  Pro  Lys  Pro  Lys  Ser
                  35                       40                      45

Gln  Thr  Glu  Gly  Asp  Phe  Glu  Glu  Ile  Pro  Asp  Glu  Tyr  Ile  Leu  Asn
             50                       55                      60

Gly
        65
```

(2) INFORMATION FOR SEQ ID NO:59:

(i) SEQUENCE CHARACTERISTICS:
        (A) LENGTH: 64 amino acids
        (B) TYPE: amino acid
        (D) TOPOLOGY: linear (ii) MOLECULE TYPE: peptide (vi) ORIGINAL SOURCE:
        (A) ORGANISM: Hirudinaria manillensis (ix) FEATURE:
        (A) NAME/KEY: Modified-site
        (B) LOCATION: 64
        (D) OTHER INFORMATION: /note="Asn-64 contains a terminal
            amide group."

(xi) SEQUENCE DESCRIPTION: SEQ ID NO:59:

| Val | Ser | Tyr | Thr | Asp | Cys | Thr | Glu | Ser | Gly | Gln | Asn | Tyr | Cys | Leu | Cys |
|---|---|---|---|---|---|---|---|---|---|---|---|---|---|---|---|
| 1 | | | | 5 | | | | | 10 | | | | | 15 | |

| Val | Gly | Ser | Asn | Val | Cys | Gly | Glu | Gly | Lys | Asn | Cys | Gln | Leu | Ser | Ser |
|---|---|---|---|---|---|---|---|---|---|---|---|---|---|---|---|
| | | | 20 | | | | | 25 | | | | | 30 | | |

| Ser | Gly | Asn | Gln | Cys | Val | His | Gly | Glu | Gly | Thr | Pro | Lys | Pro | Lys | Ser |
|---|---|---|---|---|---|---|---|---|---|---|---|---|---|---|---|
| | | 35 | | | | | 40 | | | | | 45 | | | |

| Gln | Thr | Glu | Gly | Asp | Phe | Glu | Glu | Ile | Pro | Asp | Glu | Tyr | Ile | Leu | Asn |
|---|---|---|---|---|---|---|---|---|---|---|---|---|---|---|---|
| | 50 | | | | | 55 | | | | | 60 | | | | |

ANTI-THROMBIN POLYPEPTIDES

This is a division, of application Ser. No. 07/842,089, filed on Feb. 26, 1992, now U.S. Pat. No. 5,356,875.

BACKGROUND OF THE INVENTION

1. Field of the Invention

The present invention relates to polypeptides and to their preparation. The polypeptides have been isolated from the leech *Hirudinaria manillensis*. The polypeptides have anti-thrombin properties.

2. Discussion of the Background

The most popular anticoagulant peptides are probably those belonging to the family of himdins. Hirudin, originally isolated from the medicinal leech, *Hirudo medicinalis,* is a well known and well characterized polypeptidic inhibitor of thrombin[1,2]. More particularly, it binds thrombin by ionic interactions thus preventing the cleavage of fibrinogen to fibrin and the subsequent fibrinclot formation. In animal studies hirudin has demonstrated efficacy in preventing venous thrombosis, vascular shunt occlusion and thrombin-induced disseminated intravascular coagulation. In addition, himdin exhibits low toxicity, little or no antigenicity and a very short clearance time from circulation.[3]

Polypeptides with anticoagulant properties have been isolated from a different leech species, *Hirudinaria manillensis* (EP-A-0347376 and WO 90/05143). This leech evolutionarily more advanced than *Hirudo medicinalis* and could therefore synthesize anticoagulant peptides whose amino acid sequences may be different from those of hirudin and other known hirudin variants.

We have analysed a preparation obtained from *Hirudinaria manillensis* leeches. We have found three new polypeptides having anti-thrombin activity. Accordingly, the present invention provides a polypeptide comprising the amino acid sequence:

(i) P1
Val Ser Tyr Thr Asp Cys Thr Glu Ser Gly Gln Asn Tyr Cys Leu
1                   5                        10                       15

Cys Val Gly Gly Asn Leu Cys Gly Gly Gly Lys His Cys Glu Met
                    20                        25                       30

Asp Gly Ser Gly Asn Lys Cys Val Asp Gly Glu Gly Thr Pro Lys
                    35                        40                       45

Pro Lys Ser Gln Thr Glu Gly Asp Phe Glu Glu Ile Pro Asp Glu
                    50                        55                       60

Yaa Ile Leu Asn Zaa;
                    65

(ii) P2
Val Ser Tyr Thr Asp Cys Thr Glu Ser Gly Gln Asn Tyr Cys Leu
1                   5                        10                       15

Cys Val Gly Ser Asn Val Cys Gly Glu Gly Lys Asn Cys Gln Leu
                    20                        25                       30

Ser Ser Ser Gly Asn Gln Cys Val His Gly Glu Gly Thr Pro Lys
                    35                        40                       45

Pro Lys Ser Gln Thr Glu Gly Asp Phe Glu Glu Ile Pro Asp Glu
                    50                        55                       60

Yaa Ile Leu Asn Zaa; or (iii) P3
Val Ser Tyr Thr Asp Cys Thr Glu Ser Gly Gln Asn Tyr Cys Leu
1                   5                        10                       15

Cys Val Gly Ser Asn Val Cys Gly Glu Gly Lys Asn Cys Gln Leu
                    20                        25                       30

Ser Ser Ser Gly Asn Gln Cys Val His Gly Glu Gly;
                    35                        40 and pharmaceutically acceptable salts thereof.

DETAILED DESCRIPTION OF THE PREFERRED EMBODIMENTS

Amino acid residues are presented according to the three letter code (Eur. J. Biochem. 138, 9–37, 1984). A Yaa represents an Asp (SEQ ID NOS: 1, 2, 50, 51, 55 and 56) or Tyr (SEQ ID NOS: 52, 53, 54, 57, 58 and 59) residue and Zaa is absent (SEQ ID NOS: 1, 2, 3, 52 and 57), Gly (SEQ ID NOS: 50, 53, 55 and 58) or an organic group which modifies the carboxy terminus of Asn so as to produce a primary amide ($NH_2$) (SEQ ID NOS: 51, 54, 56 and 59). The salts may be acid addition salts. They may be salts with an inorganic acid such as a hydrohalic acid, such as hydrochloric acid; sulphuric acid; phosphoric acid; or pyrophosphoric acid. The salts may be salts with an organic acid such as benzenesulphonic, p-toluenesulphonic, methanesulphonic, acetic, lactic, palmitic, stearic, malic, tartaric, ascorbic or citric acid. The polypeptides also contain free carboxyl groups and may therefore be present as sodium, calcium, potassium, magnesium or ammonium salts or salts with a physiologically tolerable organic nitrogen-containing base. The polypeptides can also be in the form of inner salts.

The polypeptides of the invention therefore consist essentially of the amino acid sequences (i) to (iii). The natural polypeptides isolated from *Hirudinaria manillensis* leeches have the amino acid sequence (i) or (ii) in which Yaa is Asp and Zaa is —OH or the partial amino acid sequence (iii). The polypeptides of the invention may be isolated and purified for use as anti-thrombin agents.

The polypeptides may be produced preceded by all or part of a leader sequence. The leader sequence may be a native or foreign leader sequence with respect to the cell in which a polypeptide is obtained. The leader sequence is capable of directing secretion of the polypeptide from the cell. Two of the natural polypeptides of the invention are expressed with a leader sequence which is cleaved subsequently. All or part of this leader sequence may therefore be present, the sequence being:
Met Phe Ser Leu Lys Leu Phe Val Val Phe Leu Ala Val Cys Ile Cys Val Ser Gln Ala.

A natural polypeptide according to the invention, or salts thereof, may be prepared by isolating the said polypeptide or a pharmaceutically acceptable salt thereof from the tissue or secretions of a leech of the species *Hirudinaria manillensis*. More specifically, a polypeptide of the invention can be obtained by obtaining a preparation according to WO 90/05143 and subjecting the preparation to high pressure liquid chromatography.

A polypeptide according to the invention or a salt thereof can also be prepared by:

(a) providing a host, transformed with an expression vector comprising a DNA sequence encoding a said polypeptide, under such conditions that the said polypeptide is expressed therein; and (b) isolating the said polypeptide thus obtained or a pharmaceutically acceptable salt thereof.

This approach is typically based on obtaining a nucleotide sequence encoding the polypeptide it is wished to express and expressing the polypeptide in recombinant organisms. The cultivation of the genetically modified organisms leads to the production of the desired product displaying full biological activity. The present invention therefore further provides an expression vector comprising a DNA sequence encoding a polypeptide of the invention;

a host transformed with a compatible expression vector according to the invention; and a DNA sequence encoding a polypeptide according to the invention.

A host in which a polypeptide according to the invention is able to be expressed is prepared by transforming a host with a compatible expression vector of the invention. The expression vector can be prepared by:

(a) chemically synthesising a DNA sequence encoding a polypeptide of the invention; and (b) inserting the said DNA into an expression vector.

Alternatively, an expression vector can be prepared by:

(a) producing and isolating a cDNA encoding the polypeptide of the invention from mRNA of a leech of the species *Hirudinaria manillensis;* and (b) inserting the isolated cDNA into an expression vector.

A polypeptide according to the invention is consequently prepared by providing a transformed host under such conditions that the polypeptide is expressed therein. When a eucaryotic host is employed, the polypeptide can be obtained glycosylated. The polypeptide can be isolated as such or in the form of a pharmaceutically acceptable salt. In this way, a polypeptide or salt according to the invention may be obtained in pure form.

The polypeptides of the invention may be modified by way of amino acid extension at either or each end. A polypeptide composed of such an extended sequence must of course still exhibit anti-thrombin activity. For example, a short sequence of up to 30 amino acid residues may be provided at either or each terminus.

The polypeptides of the invention may be subjected to one or more post-translational modification such as sulphation, COOH— amidation, acylation or chemical alteration of the polypeptide chain. For example a polypeptide having a glycine residue at its carboxy terminus may be subjected to enzymatic amidation with peptidylglycine α-amidating monooxygenase (PAM enzyme).

In order to produce an anti-thrombin polypeptide by recombinant DNA technology, a gene encoding a polypeptide of the invention is prepared. The DNA coding sequence typically does not include introns. The DNA sequence is isolated and purified. The gene is inserted in an expression vector able to drive production of the recombinant product. The DNA sequence may be a cDNA sequence. The DNA sequence may be a synthetic DNA sequence. The synthetic gene is typically prepared by chemically synthesising oligonucleotides which, in total, correspond to the desired gene. The oligonucleotides are then assembled to obtain the gene.

A gene may therefore be constructed from six chemically synthesised oligonucleotides, each oligonucleotide representing about one third of one strand of a double-stranded DNA gene. The oligonucleotides are. ligated and annealed to obtain the desired gene. If desired, the gene sequence may be modified by site-directed mutagenesis to introduce one or more codon changes. Typically, a gene is constructed with restriction sites at each end to facilitate its subsequent manipulation.

A DNA sequence may be provided which further encodes a leader peptide as mentioned above. The leader peptide is capable of directing secretion of the polypeptide from cells in which the polypeptide is to be expressed. The sequence encoding the leader peptide is typically fused to the 5'-end of the DNA sequence encoding the polypeptide.

The leader peptide may be the OmpA leader peptide when expression in a bacterial host, such as *E. coli* is required. The leader peptide may be the leader peptide of vesicular stomatitis virus G protein (VSV G protein) when expression is to be in insect cells. Appropriate DNA sequences encoding the OmpA and VSV G protein leader sequences are:

```
OmpA leader:
ATG AAA AAG ACA GCT ATC GCG ATT GCA GTG GCA CTG GCT GGT    42
TTC GCT ACC GTA GCG CAG GCC                                 63

VSV G protein leader:
ATG AAG TGC CTT TTG TAC TTA GCC TTT TTA TTC ATT GGG GTG    42
AAT TGC                                                     48
```

A DNA sequence may be provided which encodes a fusion protein which is cleavable to release a polypeptide of the invention. A DNA sequence may be used which encodes a carrier polypeptide sequence fused via a cleavable linkage to the N-terminus of a polypeptide of the invention. The cleavable linkage may be one cleavable by cyanogen bromide.

For expression of the polypeptide, an expression vector is constructed which comprises a DNA sequence encoding the polypeptide and which is capable of expressing the polypeptide when provided in a suitable host. Appropriate transcriptional and translational control elements are provided, including a promoter for the DNA sequence, a transcriptional termination site, and translational start and stop codons. The DNA sequence is provided in the correct frame such as to enable expression of the polypeptide to occur in a host compatible with the vector.

The expression vector typically comprises an origin of replication and, if desired, a selectable marker gene such as an antibiotic resistance gene. A promoter is operably linked to the DNA sequence encoding the polypeptide. The expression vector may be a plasmid. In that case, preferably a promoter selected from the $P_{trp}$ and $P_{lcc/lac}$ promoters is operably linked to the DNA sequence. Alternatively, the expression vector may be a virus. The virus may be a recombinant baculovirus in which the polyhedrin promoter is operably linked to the DNA sequence encoding the polypeptide.

An expression vector capable of expressing the polypeptide may be prepared in any convenient fashion. A DNA fragment encoding the polypeptide may be inserted into an appropriate restriction site of an expression vector, for example a plasmid vector. A recombinant baculovirus may be prepared by:

(i) cloning a gene encoding the polypeptide into a baculovirus transfer vector at a restriction site downstream of the polyhedrin promoter; and (ii) co-transfecting insect cells susceptible to baculovirus infection with the recombinant transfer vector from step (i) and intact wild-type baculovirus DNA.

Homologous recombination occurs, resulting in a recombinant baculovirus harbouring the polypeptide gene downstream of the polyhedrin promoter. The baculovirus transfer vector may be one having a unique cloning site downstream of the polyhedrin ATG start codon. The product that is then expressed by the resulting recombinant baculovirus will be a fusion protein in which a N-terminal portion of the polyhedrin protein is fused to the N-terminus of the polypeptide. As indicated above, a cleavable linkage may be provided at the fusion junction.

The insect cells employed in step (ii) are typically *Spodoptera frugiperda* cells. The wild-type baculovirus is typically *Autographa californica* nuclear polyhedrosis virus (AcNPV).

An expression vector encoding the polypeptide is provided in an appropriate host. Cells are transformed with the polypeptide gene. A transformed host is provided under such conditions that the polypeptide is expressed therein. Transformed cells, for example, are cultivated so as to enable expression to occur. Any compatible host-vector system may be employed.

The transformed host may be a prokaryotic or eukaryotic host. A bacterial or yeast host may be employed, for example *E. coli* or *S. Cerevisiae*. Gram positive bacteria may be employed. A preferred bacterial host is a strain of *E. coli* type B. Insect cells can alternatively be used, in which case a baculovirus expression system is appropriate. The insect cells are typically *Spodoptera frugiperda* cells. As a further alternative, cells of a mammalian cell line may be transformed. A transgenic animal, for example a non-human mammal, may be provided in which the polypeptide is produced.

The polypeptide that is expressed may be isolated and purified. A polypeptide having any one of the amino acid sequences (i), (ii) or (iii) above preceded by a Met residue attributable to a translation start codon can be obtained. Alternatively, as mentioned above, a fusion protein may be obtained comprising the amino acid sequence of a polypeptide of the invention, i.e. sequence (i), (ii) or (iii) above, fused to a carrier sequence. Where a suitable linkage is provided in the fusion protein between the amino acid sequence (i), (ii) or (iii) and the carrier sequence, a polypeptide having amino acid sequence (i), (ii) or (iii) can be released by cleavage with a suitable agent.

A polypeptide of the invention or a pharmaceutically acceptable salt thereof can also be prepared by:

(a) chemically synthesising the said polypeptide; and
(b) isolating the said polypeptide thus obtained or a pharmaceutically acceptable salt thereof.

The polypeptides can therefore be built up by chemical synthesis from single amino acids and/or preformed peptides of two or more amino acids in the order of the sequence of the desired polypeptide. Solid-phase or solution methods may be employed. The resultant polypeptide may be converted into a pharmaceutically acceptable salt if desired.

In solid-phase synthesis, the amino acid sequence of the desired polypeptide is built up sequentially from the C-terminal amino acid which is bound to an insoluble resin. When the desired polypeptide has been produced, it is cleaved from the resin. When solution-phase synthesis is employed, the desired polypeptide may again be built up from the C-terminal amino acid. The carboxy group of this acid remains blocked throughout by a suitable protecting group, which is removed at the end of the synthesis.

Whichever technique, solid-phase or solution-phase, is employed each amino acid added to the reaction system typically has a protected amino group and an activated carboxy group. Functional side-chain groups are protected too. After each step in the synthesis, the amino-protecting group is removed. Side-chain functional groups are generally removed at the end of the synthesis.

A polypeptide may be converted into a pharmaceutically acceptable salt. It may be converted into an acid addition salt with an organic or inorganic acid. Suitable acids include acetic, succinic and hydrochloric acid. Alternatively, the peptide may be converted into a carboxylic acid salt such as the ammonium salt or an alkali metal salt such as the sodium or potassium salt.

A polypeptide or pharmaceutically acceptable salt thereof may be used in a pharmaceutical composition, together with a pharmaceutically acceptable carrier or excipient therefor. Such a formulation is typically for intravenous administration (in which case the carrier is generally sterile saline or water of acceptable purity). A polypeptide according to the invention is an anti-thrombin and is suitable for treatment of thromboembolic events, such as the coagulation of blood, typically in a human patient. A polypeptide can therefore be used for the therapy and prophylaxis of thromboses and thromboembolisms, including the prophylaxis of post-operative thromboses, for acute shock therapy (for example for septic or polytraumatic shock), for the therapy of consumption coagulopathies, in haemodialyses, haemoseparations and in extracorporeal blood circulation. In one embodiment of the invention, the polypeptide or salt thereof can be coadministered with a plasminogen activator, such as tissue plasminogen activator.

The dosage depends especially on the specific form of administration and on the purpose of the therapy or prophylaxis. The size of the individual doses and the administration regime can best be determined by way of an individual judgement of the particular case of illness; the methods of determining relevant blood factors required for this purpose are familiar to the person skilled in the art. Normally, in the case of an injection the therapeutically effective amount of the compounds according to the invention is in a dosage range of from approximately 0.005 to approximately 0.1 mg/kg body weight. A range of from approximately 0.01 to approximately 0.05 mg/kg body weight is preferred. The administration is effected by intravenous, intramuscular or subcutaneous injection. Accordingly, pharmaceutical compositions for parenteral administration in single dose form contain per dose, depending on the mode of administration, from approximately 0.4 to approximately 7.5 mg of the compound according to the invention. In addition to the active ingredient these pharmaceutical compositions usually also contain a buffer, for example a phosphate buffer, which is intended to keep the pH value between approximately 3.5 and 7, and also sodium chloride, mannitol or sorbitol for adjusting the isotonicity. They may be in freeze-dried or dissolved form, it being possible for solutions advantageously to contain an antibacterially active preservative, for example from 0.2 to 0.3% 4-hydroxybenzoic acid methyl ester or ethyl ester.

A composition for topical application can be in the form of an aqueous solution, lotion or gel, an oily solution or suspension or a fat-containing or, especially, emulsified ointment. A composition in the form of an aqueous solution is obtained, for example, by dissolving the active ingredients according to the invention, or a therapeutically acceptable salt thereof, in an aqueous buffer solution of from e.g., pH 4 to pH 6.5 and, if desired, adding a further active ingredient, for example an anti-inflammatory agent, and/or a polymeric binder, for example polyvinylpyrrolidone, and/or a preservative. The concentration of active ingredient is from approximately 0.1 to approximately 1.5 mg, preferably from 0.25 to 1.0 mg, in 10 ml of a solution or 10 g of a gel.

An oily form of administration for topical application is obtained, for example, by suspending the active ingredient according to the invention, or a therapeutically acceptable salt thereof, in an oil, optionally with the addition of swelling agents, such as aluminium stearate, and/or surfactants (tensides) having an HLB value ("hydrophilic-lipophilic balance") of below 10, such as fatty acid monoesters of polyhydric alcohols, for example glycerin monostearate, sorbitan monolaurate, sorbitan monostearate or sorbitan monooleate. A fat-containing ointment is obtained, for example, by suspending the active ingredient according to the invention, or a salt thereof, in a spreadable fatty base, optionally with the addition of a tenside having an HLB value of below 10. An emulsified ointment is obtained by triturating an aqueous solution of the active ingredient according to the invention, or a salt thereof, in a soft, spreadable fatty base with the addition of a tenside having an HLB value of below 10. All these forms for topical application can also contain preservatives. The concentration of active ingredient is from approximately 0.1 to approximately 1.5 mg, preferably from 0.25 to 1.0 mg, in approximately 10 g of base.

In addition to the compositions described above and pharmaceutical compositions analogous thereto that are intended for direct medicinal use in the body of a human or a mammal, the present invention relates also to pharmaceutical compositions and preparations for medicinal use outside the living body of humans or mammals. Such compositions and preparations are used especially as anticoagulant additives to blood that is being subjected to circulation or treatment outside the body (for example extracorporeal circulation or dialysis in artificial kidneys), preservation or modification (for example haemoseparation). Such preparations, such as stock solutions or alternatively preparations in single dose form, are similar in composition to the injection preparations described above; however, the amount or concentration of active ingredient is advantageously based on the volume of blood to be treated or, more precisely, on its thrombin content. In this connection it must be borne in mind that the active ingredient according to the invention (in free form) completely deactivates approximately 5 times the amount by weight of thrombin, are physiologically harmless even in relatively large amounts, and are eliminated from the circulating blood rapidly even in high concentrations so that there is no risk of overdose, even, for example, during transfusions. Depending on the specific purpose, the suitable dose is from approximately 0.01 to approximately 1.0 mg of the active ingredient/liter of blood, although the upper limit may still be exceeded without risk.

The following Examples illustrate the invention.

BRIEF DESCRIPTION OF THE DRAWINGS

In the accompanying drawings:

FIG. 3 shows the nucleotide sequence of the six oligonucleotides coding for most of the protein corresponding to peak 2 (P2) in which the amino acid residue in position 61 is Asp and the last amino acid of the polypeptidic chain is $Asn_{64}$. The sequence shown in bold face indicates the BalI site which has been used for further constructions. The lower part of the Figure shows the mode of assembling of the six oligos. HindIII and PstI sites were included to allow subsequent manipulations.

FIG. 8 shows the nucleotide sequence and assembling of the synthetic oligos used for the secretion of P2 from insect cells. The sequence shown in bold face indicates the VSV G protein leader peptide.

EXAMPLES

Example 1

Figure 1:
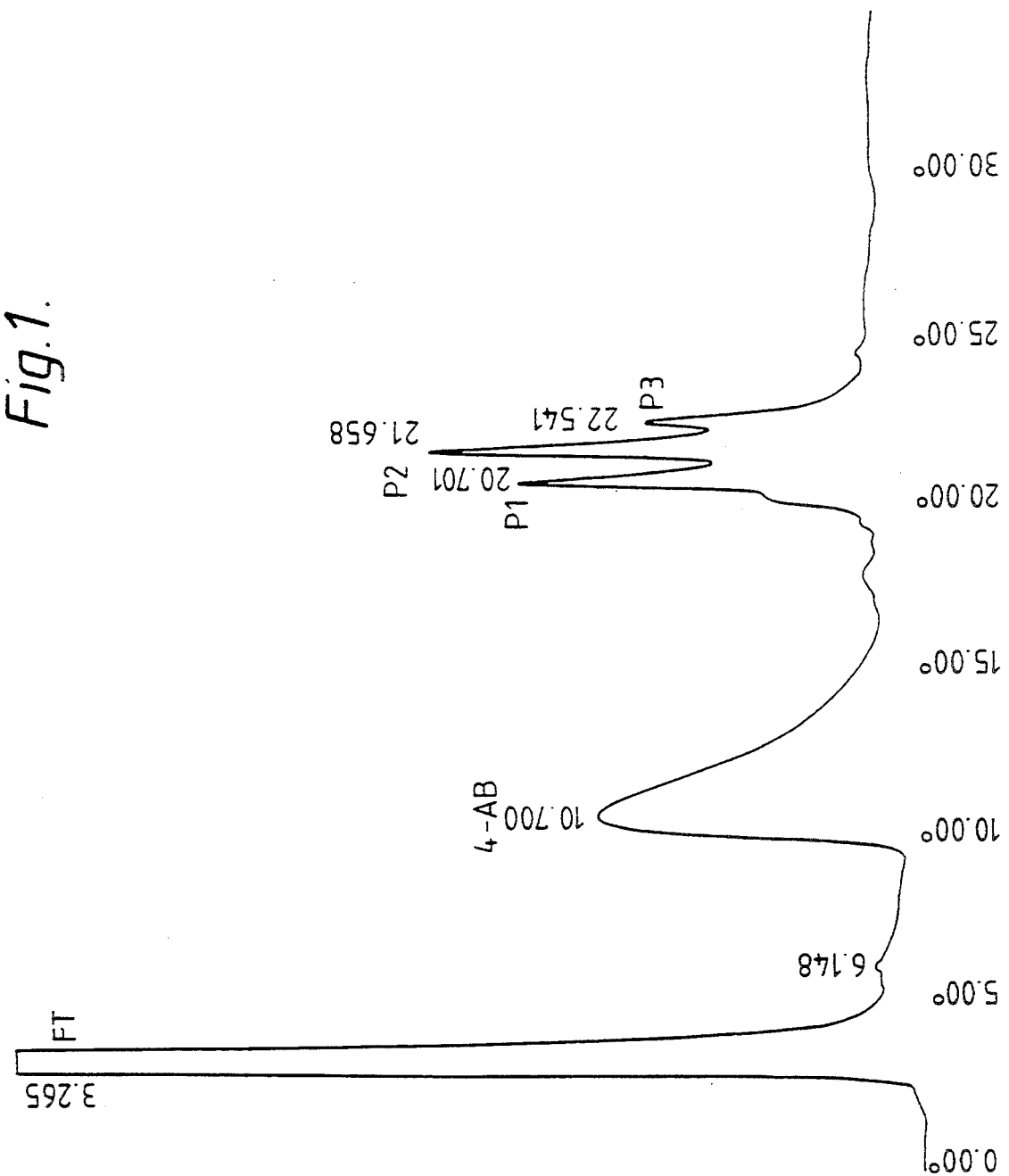
FIG. 1 is a chromatogram showing the results of the HPLC analysis of Example 1. P1 to P3 denote the three different peaks obtained from the preparation according to Example 1, FT is for flow through and 4-AB is for 4-aminobenzamidine.

An antithrombin preparation was prepared from *Hirudinaria manillensis* leeches according to WO 90/05143, following the procedure illustrated under a) and b) below:

a) Acetone extraction

Ethanol dried leech heads (2920 g) were finely chopped into small pieces and treated with a mixture 40:60 acetone/water (7.5 l). After homogenisation with stirring at room temperature, the mixture was spun for 15 min at 2,700 rpm and the supernatant was decanted; the pellet was again resuspended in 40:60 acetone:water mixture, stirred for 30 min and the mixture centrifuged for 15 min at 2,700 rpm. The supernatant was pooled with the initial one and acidified to pH 4.5 with glacial acetic acid (vol. 8.5 l). The mixture was spun at 2,700 rpm for 15 minutes, then the supernatant was decanted and the pH of the solution adjusted to pH 6.0 by adding 30% ammonia. Following rotary evaporation at 35° C., the pH of the concentrated solution was lowered to 1.8; precipitated contaminants were removed by centrifuging and the raw anti-thrombin material was precipitated from the mixture using a 9-fold acetone excess. The mixture was then spun down, the pellet resuspended in acetone and again centrifuged. The precipitated material was then lyophilized.

b) Ionic exchange purification

The raw anti-thrombin material was reconstituted in water, dialyzed against 10 mM ammonium acetate buffer at pH 4.0 and loaded onto a carboxymethyl Sepharose column (CM Sepharose, Pharmacia, 2.6×30 cm) pre-equilibrated in the same buffer. Following a 100 ml washing with starting buffer, anti-thrombin active fractions were eluted with 20 mM ammonium acetate pH 4.5, collected and pooled (1.3 l). For further purification steps, pooled fractions were concentrated to 0.5 l in a Minitan apparatus (Millipore); the concentrated solution was neutralised with NaOH and then applied on to a Q Sepharose column equilibrated in 20 mM Tris-HCl pH 7.0. The bound material was eluted with a linear gradient of 0–1M NaCl in the starting buffer. The fractions containing with anti-thrombin activity were pooled, concentrated and desalted on a Superdex S-200 column eluted with 20 mM Tris-HCl pH 7.5 at a flow rate of 4 ml/min. Active pool from gel filtration was concentrated by Minitan and further purified by weak anion exchange chromatography (DEAE FPLC). The active material was loaded onto a Protein Pak DEAE-5PW column (Waters) and eluted with a gradient of 0–1M NaCl in 20 mM Tris-HCl pH 6.5, at a flow rate of 1.0 ml/min. Active fractions were pooled, characterized for protein content and activity (specific activity: 800 ATU/mg), and freeze-dried in a SpeedVac concentrator (Savant).

The thus obtained partially purified material (specific activity 800 ATU/mg) was then subject to two additional chromatographic steps, in order to get homogenous polypeptides, as described below under c) and d):

c) Thrombin-Sepharose

Commercial bovine thrombin (Sigma) was further purified according to the procedure described by Lundblad (*) and then was attached to activated Sepharose CL 6B (Pharmacia) following manufacturer's instructions. The column (1.7 ml) was equilibrated with 50 mM Tris-HCl pH 8.3 and the freeze-dried material from DEAE-FPLC (reconstituted in buffer) was loaded. The column was subjected to three washing, in starting buffer, then in the same buffer containing 3.0 M NaCl and again with starting buffer (each washing was three times the column volume). Flow rate was 0.3 ml/min. The bound material was eluted with 10 ml of 0.1 M 4-aminobenzamidine in 25 mM HCl. The active fractions were pooled and buffer exchanged in 50 mMTris-HCl pH 8.3 onto a PD-10 column (Pharmacia).

Unbound material eluted from the column by washing in starting buffer and still containing anti-thrombin activity, was reloaded onto the column until all the activity was bound and chromatographed. (*) Lundblad, R. L., 1971, Biochemistry, 10:2501–2506 d) RP-HPLC

Material obtained after affinity chromatography was finally purified by reverse phase high performance chromatography (RP-HPLC) on a C4 Vydac column (4.6×250 mm. 5μ) using 20 mM sodium phosphate pH 7.5 as first eluent and 50% acetonitrile in water as modified. Anti-thrombin polypeptides were eluted with a linear gradient from 5% to 55% of eluent B in 45 minutes, at room temperature with a flow rate of 1.0 ml/min. The resulting chromatogram is shown in FIG. 1.

Peaks of protein (detected at 220 nm) were manually collected, concentrated under vacuum and rechromatographed under the same conditions.

Pure anti-thrombin polypeptides after C4 HPLC were characterized for protein content, amino acid composition, N-terminal sequence, C-terminal end and their activity determined by in vitro assays (ATU/NIH test and "thrombin time" test). Each of the three peaks of protein has been found to be endowed with anti-thrombin activity, The complete amino acid sequences-of the polypeptides labeled P1 and P2 in FIG. 1 were determined by N-terminal sequencing of the peptides obtained from tryptic and V8 protease digests. The sequences are reported under (i) and (ii) above. The partial amino acid sequence of the other polypeptide (P3) is reported under (iii) above.

Example 2—Tryptic digestion and peptide mapping of pyridylethylated (PE) P1 and P2 a) Reduction/Alkylation—Active fractions purified by affinity chromatography on Thrombin-Sepharose (Example 1c) were pooled and buffer exchanged in 10 mM Tris-HCl pH 8.3 onto a PD-10 column. The active pool (about 50 μg) was concentrated in a Speed-Vac centrifuge (Savant) and treated with 100 μl of 1% b-mercaptoethanol in 6M guanidine-HCl/50 mM Tris-HCl pH 8.5, under nitrogen, in the dark, for 2 hours at room temperature. Then 4 μl of 4-vinylpyridine (neat) were added and the mixture incubated again for 2 hours as above[4].

Pyridylethylated polypeptides were first recovered from the reaction mixture by RP-HPLC on a C4 Vydac (4.6×250 mm, 5 μm) column eluted with a 90 min. linear gradient from 5–65% acetonitrile in 0.1% TFA, at a flow rate of 1.0 ml/min. Under such conditions the mixture of anti-thrombin polypeptides is poorly resolved so that they have to be re-chromatographed on the same column using the elution system sodium phosphate/acetonitrile with the conditions already described in Example 1d.

b) Trypsin digestion and peptide mapping of PE-P1 and PE-P2.—Purified PE-P1 and PE-P2 (respectively 10 and 20 μg) were digested with TPCK-treated trypsin (Sigma) in 200 μl of 1% ammonium bicarbonate pH 8.0 in the presence of 0.2M sodium phosphate. Trypsin was added at an enzyme-to-substrate ratio of 1:20 (w/w) and incubation was carried out for 4 hours at 37° C. Digestion was stopped by freeze-drying in Savant.

Figure 2A:
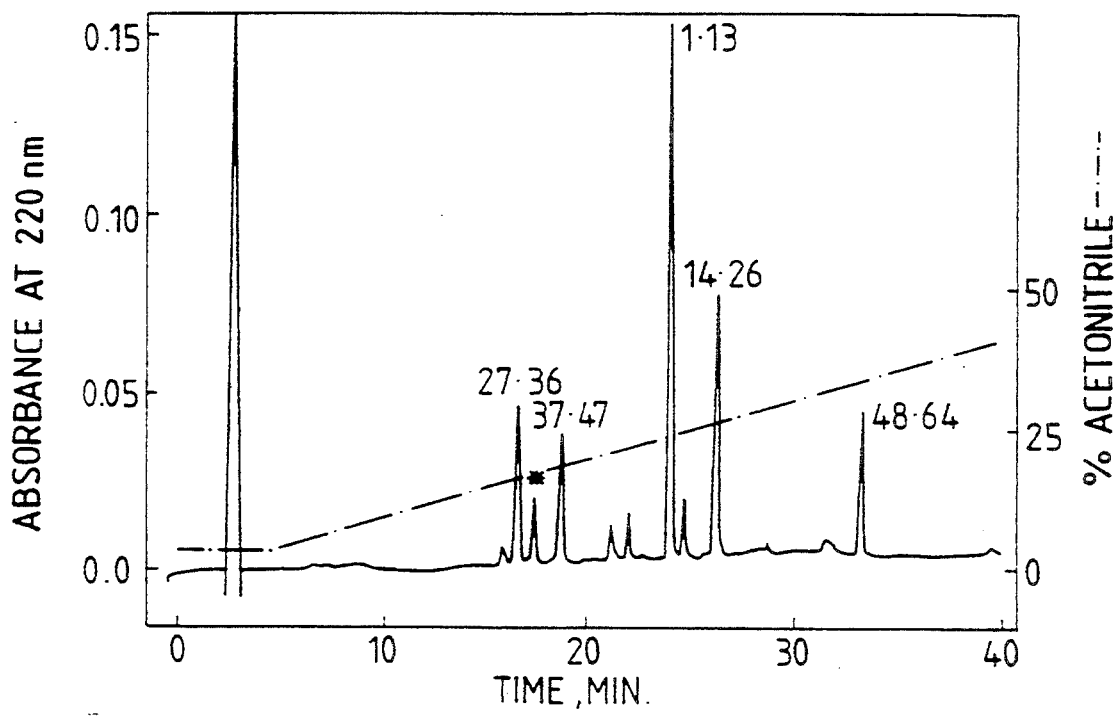
FIG. 2 shows the elution profiles obtained in Example 2(b) for trypsin-digested PE-P1 (A) and PE-P2 (B).
Figure 2B:
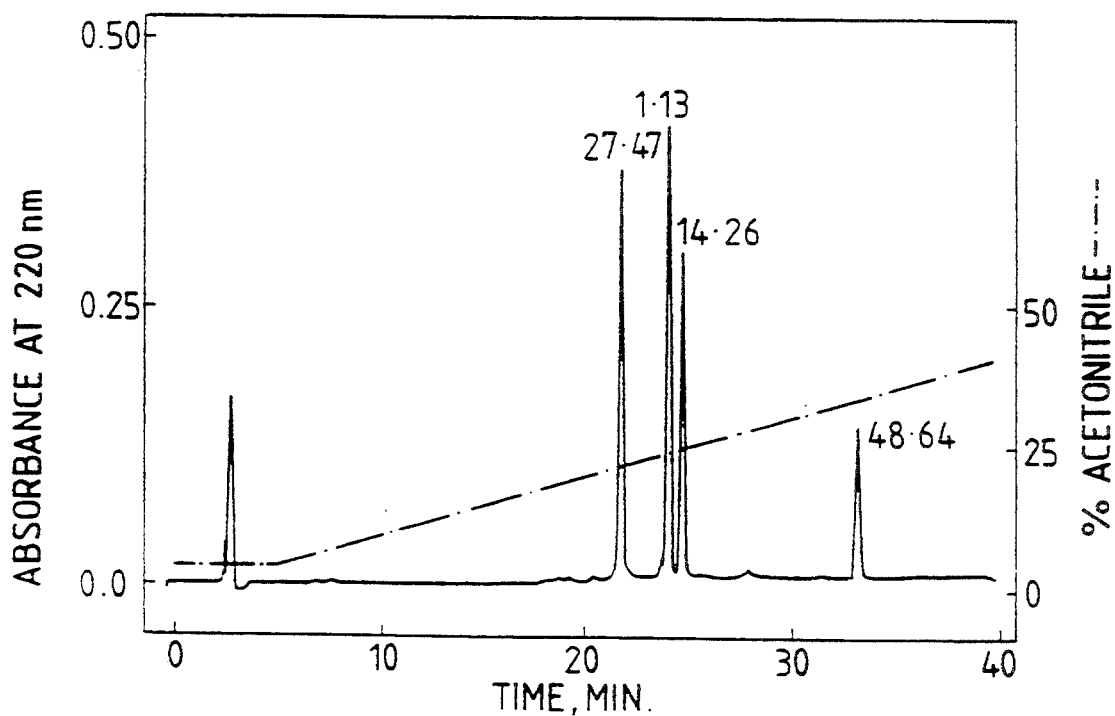

Peptides obtained by tryptic digestion were separated on a μBondapak C18 column (3.9×300 mm, 10μ Waters) or on a C4-Vydac (4.6×250 mm, 5 μm) column eluted using a 60 min. linear gradient from 5–65% acetonitrilein 0.1% TFA, at a flow rate of 1.0 ml/min (FIG. 2). Eluted peaks were manually collected, concentrated in Savant and then subjected to amino acid analysis and to N-terminal sequence analysis on a pulsed liquid-phase mod. 477A Sequencer (Applied Biosystems).

The results of C4-HPLC peptide mapping of trypsin-digested PE-P1 (A) and PE-P2 (B) are shown below.

recombinant P2 protein in bacterial and insect cells. In the case of insect cells methods were developed which yielded protein P2 as a secreted or cytoplasmic product.

All plasmid DNA manipulations were carried out as described by Maniatis et al[6].

Figure 4:
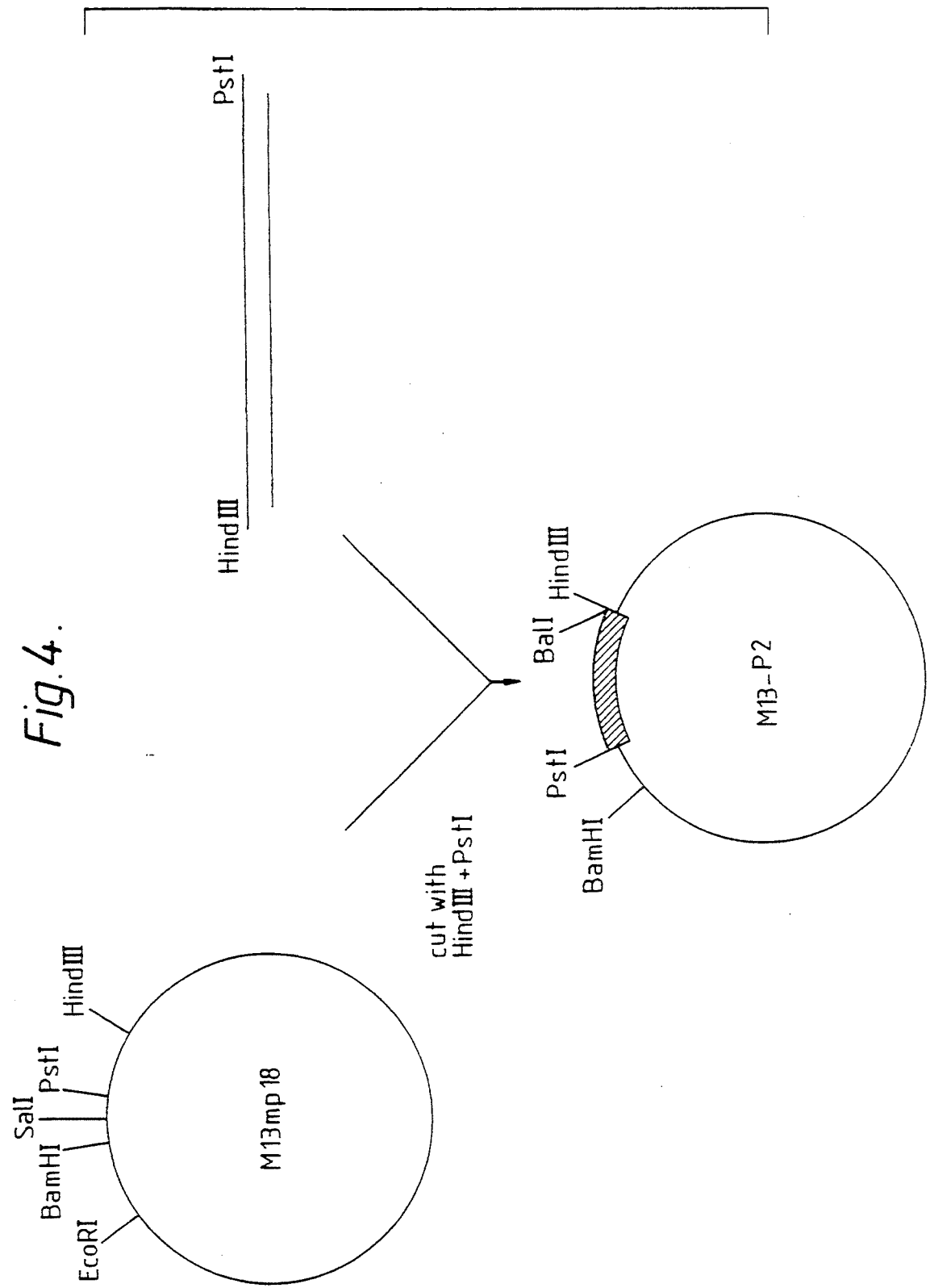
FIG. 4 shows the scheme of the construction of the intermediate plasmid M13-P2, which is the source of a BalI-BamHI DNA fragment for all further P2 constructions.

Six synthetic complementary oligonucleotides were prepared using an automated DNA synthetizer (Applied Biosystems) and their sequence is shown in FIG. 3. Following enzymatic phosphorylation the six oligos were assembled using DNA ligase and the resulting double-strand sequence was inserted in the M13 phage vector mp18, obtaining the recombinant plasmid M13-P2 which is shown in FIG. 4. In order to enable insertion of the P2 gene in the M13 vector, HindIII and PstI sites were also added in the synthetic oligos. The correct nucleotide sequence has been verified by the Sanger method carried out on the single strand phage DNA[7].

The recombinant plasmid M13-P2 was used as the source of the P2 gene for all the expression vectors used in the Examples.

Example 4: Expression and secretion of P2 from *E. coli* cells

In order to obtain secretion to the periplasm of the recombinant product, it is necessary to synthesize the P2 molecule in the form of a pre-protein. More particularly, an amino acid sequence named "leader peptide", responsible for an efficient secretion must be present at the $NH_2$ end of P2 8,9. This extra sequence is then cleaved off, in vivo, during secretion, by a specific *E. coli* leader peptidase, yielding the correct mature sequence[10].

|   | Fragment | Amino acid sequence |   |
|---|----------|---------------------|---|
| A | 1-13     | VSYTDCTESGQNY       | (SEQ ID NO: 13) |
|   | 14-26    | CLCVGGNLCGGGK       | (SEQ ID NO: 14) |
|   | 27-36    | HCEMDGSGNK          | (SEQ ID NO: 15) |
|   | 37-47    | CVDGEGTPKPK         | (SEQ ID NO: 16) |
|   | 37-47(*) | CVDGEGX*PKPK        | (SEQ ID NO: 17) |
|   | 48-64    | SQTEGDFEEIPDEDILN   | (SEQ ID NO: 18) |
| B | 1-13     | VSYTDCTESGQNY       | (SEQ ID NO: 19) |
|   | 14-26    | CLCVGSNVCGEGK       | (SEQ ID NO: 20) |
|   | 27-47    | NCQLSSSGNQCVHGEGX*PKPK | (SEQ ID NO. 21) |
|   | 48-64    | SQTEGDFEEIPDEDILN   | (SEQ ID NO: 22) |

(*) X = residue not detected by amino acid sequencing; X = T by amino acid analysis.

The complete amino acid sequences of P1 and P2 are therefore:

P1 (SEQ ID NO: 1)
Val Ser Tyr Thr Asp Cys Thr Glu Ser Gly Gln Asn Tyr Cys Leu
Cys Val Gly Gly Asn Leu Cys Gly Gly Lys His Cys Glu Met
Asp Gly Ser Gly Asn Lys Cys Val Asp Gly Glu Gly Thr Pro Lys
Pro Lys Ser Gln Thr Glu Gly Asp Phe Glu Glu Ile Pro Asp Glu
Asp Ile Leu Asn

P2
Val Ser Tyr Thr Asp Cys Thr Glu Ser Gly Gln Asn Tyr Cys Leu
Cys Val Gly Ser Asn Val Cys Gly Glu Gly Lys Asn Cys Gln Leu
Ser Ser Ser Gly Asn Gln Cys Val His Gly Glu Gly Thr Pro Lys
Pro Lys Ser Gln Thr Glu Gly Asp Phe Glu Glu Ile Pro Asp Glu
Asp Ile Leu Asn

Example 3: Chemical synthesis of the P2 gene

The nucleotide coding sequence was designed on the basis of the *Escherichia coli* preferred codons[5]. Moreover, a BalI restriction site was engineered very close to the 5' end of the synthetic gene to allow insertion of such sequence in different expression vectors. Indeed, the same synthetic gene was used for expression of Many examples of secretion systems have been described in the literature[11,12]. Among them, we have selected the system based on the secretion signal of the Outer Membrane Protein of *E. coli* (Omp A) previously published[13]. We therefore designed two additional complementary oligonucleotides coding for the OmpA leader peptide preceded by the OmpA Shine-Dalgarno sequence known to be responsible for an efficient translation of the messenger RNA[14].

Figure 5:
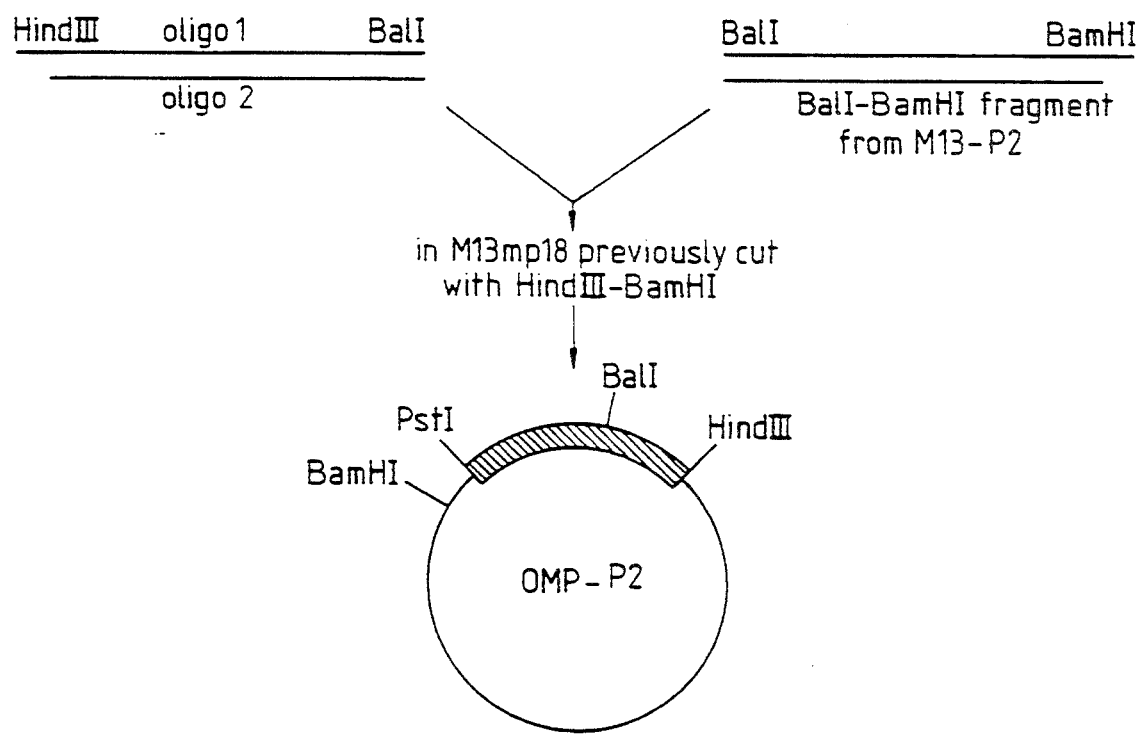
FIG. 5 shows schematically the construction of a new recombinant M13, named OMP-P2, which carries the complete P2 gene linked to the OmpA leader peptide. The leader peptide sequence is shown in bold face while the BalI blunt end and the HindIII sticky end are underlined. See SEQ ID NOS: 29–30.

Their sequence, shown in FIG. 5, includes also the beginning of the P2 gene coding for the first 10 amino acids. The presence of the BalI site allowed the joining of this synthetic piece to the rest of the P2 coding sequence while the presence of the upstream HindIII site allowed the joining to the M13 vector. Thus, the synthetic HindIII-BalI fragment was ligated to a BalI-BamHI piece from M13-P2 and inserted in M13mp18, obtaining a new plasmid named OMP-P2. The schematic representation of this new plasmid construction is also shown in FIG. 5. SEQ ID NO 46 is a synthetic nucleotide sequence encoding P2. It can be obtained by joining the coding region of the synthetic oligonucleotides disclosed in FIGS. 3 and 5 according to the procedures described in Examples 3 and 4.

From OMP-P2 the P2 gene can be excised as a HindIII-BamHI fragment which codes for the OmpA Shine-Dalgarno and leader peptide followed by the P2 coding sequence. This restriction fragment is now ready to be inserted in an appropriate expression vector. Several expression systems could, theoretically, be employed to obtain high level production of heterologous proteins in bacteria. The system based on the promoter $P_{trp}$ has been used with success in our laboratory in the past[14]. Again, even in the case of the selected promoter, the levels of expression of a given polypeptide cannot be predicted.

Figure 6:
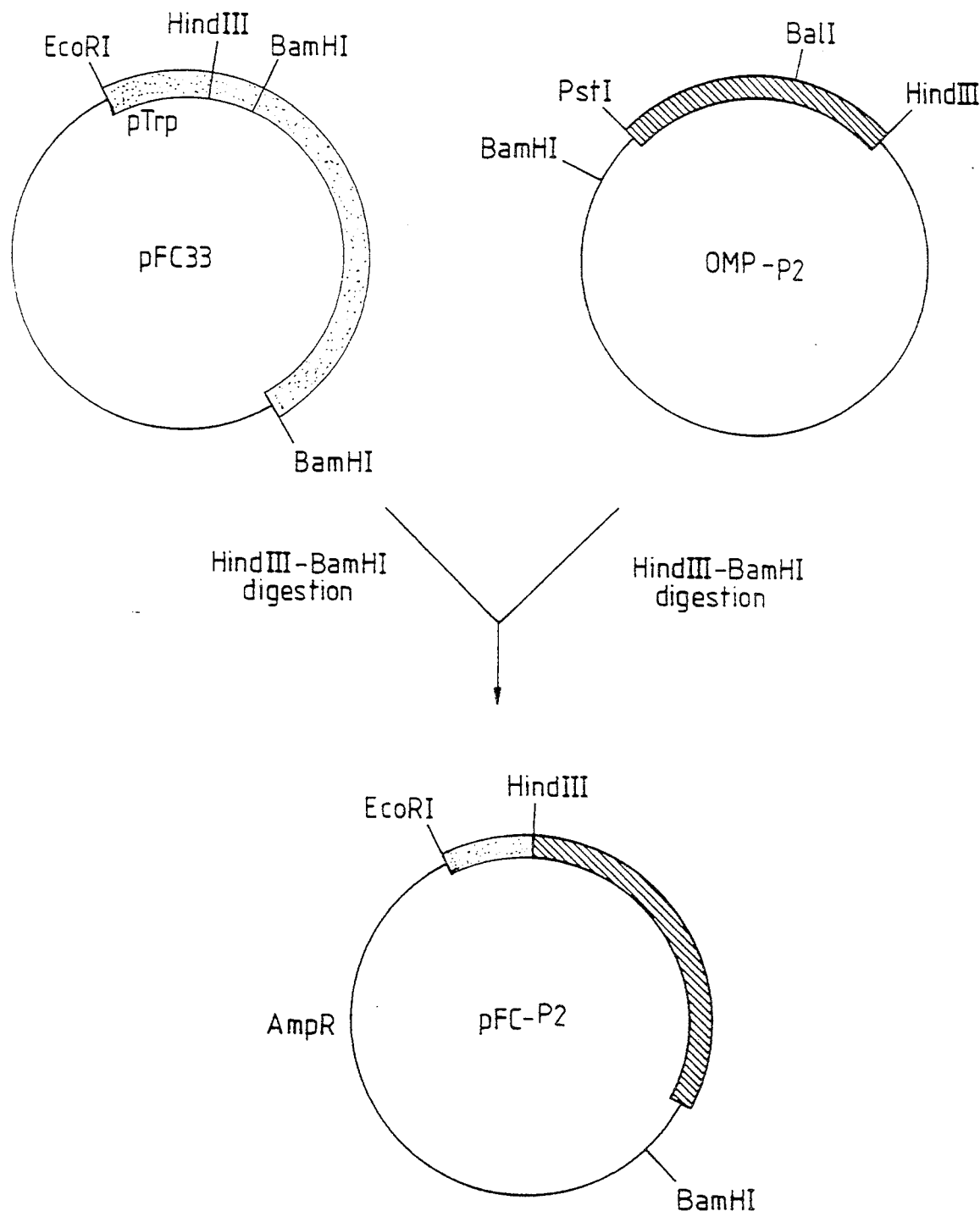
FIG. 6 shows schematically the construction of pFC-P2 which is the plasmid used for the production of P2 protein in *E. coli*.

Plasmid pFC33, shown in FIG. 6, has already been described in the literature[14]. It carries the resistance to the antibiotic ampicillin and the bacterial promoter $P_{trp}$ which drives expression of proapolipoprotein A1. Following digestion of pFC33 with HindIII and BamHI, the large HindIII-BamHI fragment, carrying the antibiotic resistance gene and the promoter, was isolated and joined to the HindIII-BamHI fragment from OMP-P2 coding for the P2 gene. The details of this construction are shown in FIG. 6. We isolated a new plasmid, named pFC-P2, which is the final plasmid for the production of P2 in E. coli.

An object of the present invention is the use of E. coli strains of the type B for the expression and secretion to the periplasm of P2 and the other anti-thrombin polypeptides of the invention. Indeed, we have found that insertion of plasmid pFC-P2 in type B strains of the bacterium E. coli brings high level production of P2. Interestingly, different strain types of E. coli do not work as efficiently and it seems, therefore, that the host strain type is crucial for the successful production of bufrudin.

Several type B strains of E. coli are available and can be used for the production of P2. Preferred strains are ATCC 12407, ATCC 11303, NCTC 10537. Below is an example of transformation of strain NCTC 10537 with plasmid pFC-P2 and subsequent cultivation of the transformant.

Competent cells of strain NCTC 10537 were prepared using the calcium chloride procedure of Mandel and Higa[15]. Approximately 200 μl of a preparation of these cells at $1 \times 10^9$ cells per milliliter were transformed with 2 μl of plasmid DNA (approximate concentration 5 μg/ml). Transformants were selected on plates of L-agar containing 100 μg/ml ampicillin. Two small colonies were streaked with wooden tooth picks (each as three streaks about 1 cm long) onto L-agar containing the same antibiotic. After 12 hours incubation at 37° C., portions of the streaks were tested for P2 protein production by inoculation onto 10 ml of LB medium (containing ampicillin at a concentration of 150 μg/ml) and incubated overnight at 37° C. The following day the cultures were diluted 1:100 in M9 medium, containing the same concentration of ampicillin, and incubated for 6 hours at 37° C.

20 ml of such culture were centrifuged at 12000×g, 4° C. for 10 minutes The bacterial pellet was resuspended in 2 ml of 33 mM HCl Tris pH 8; an equal volume of a second solution 33 mM EDTA, 40% sucrose was then added and the total mixture was incubated under mild shaking conditions at 37° C. for 10 minutes. Following centrifugation, the permeabilized cells were resuspended in 2 ml of cold water and left for 10 minutes in ice. The resulting supernatant was isolated by centrifugation and represents the periplasmic fraction of the bacterial cell.

Using a chromogenic assay that is based on the inhibition of the thrombin ability to cleave a synthetic substrate S-2238[16] we have measured the presence of anti-thrombin activity in the periplasmic fraction of P2 producing cells but not in control periplasmic fractions.

Figure 7:
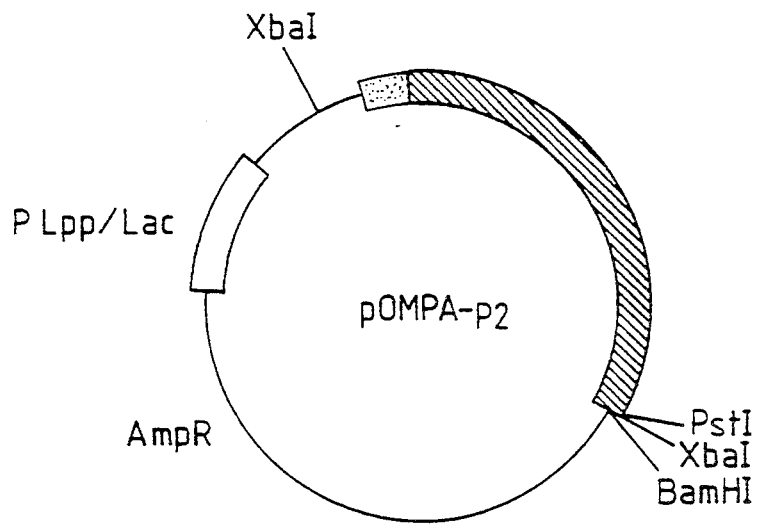
FIG. 7 shows the general structure of the plasmid pOMPA-P2 used for the production of P2 in *E. coli*. We employed traditional gene manipulation techniques to prepare this new plasmid where the P2 gene is under transcriptional control of the hybrid promoter $P_{lpp/lac}$. Even in this case, the OmpA leader peptide drives secretion of P2 to the periplasm of *E. coli*.

With the similar approach we have also constructed a new expression/secretion plasmid for P2 where the promoter $P_{lpp/lac}$[17] is present instead of the promoter $P_{trp}$. This different plasmid, named pOMP-P2, is shown in FIG. 7. Following insertion of this plasmid in E. coli strains of the type B, high levels of active P2 were also obtained. As starting plasmid for the construction of pOMP-P2 we used the plasmid pIN-III-ompA3 described by Ghrayb et al[17]. Conditions for cultivation and induction of expression with isopropyl-β-D-thiogalactopyranoside (IPTG) were as previously described[17].

Example 5: Expression and secretion of protein P2 from insect cells

To obtain secretion of protein P2 from recombinant insect cells we had to join the P2 coding sequence to a leader peptide that is efficiently recognized by these cells. We have used the leader peptide of the Vescicular Stomatitis Virus (VSV) G protein[18]. Similarly to what is described above, a synthetic DNA sequence coding for the VSV G protein leader peptide followed by the beginning of the P2 gene has been prepared and the nucleotide sequence is given in FIG. 8. Also in this case we provided convenient restriction sites (HindIII, BamHI and BalI) to allow joining to the rest of the P2 gene and to the expression vector.

Figure 9:
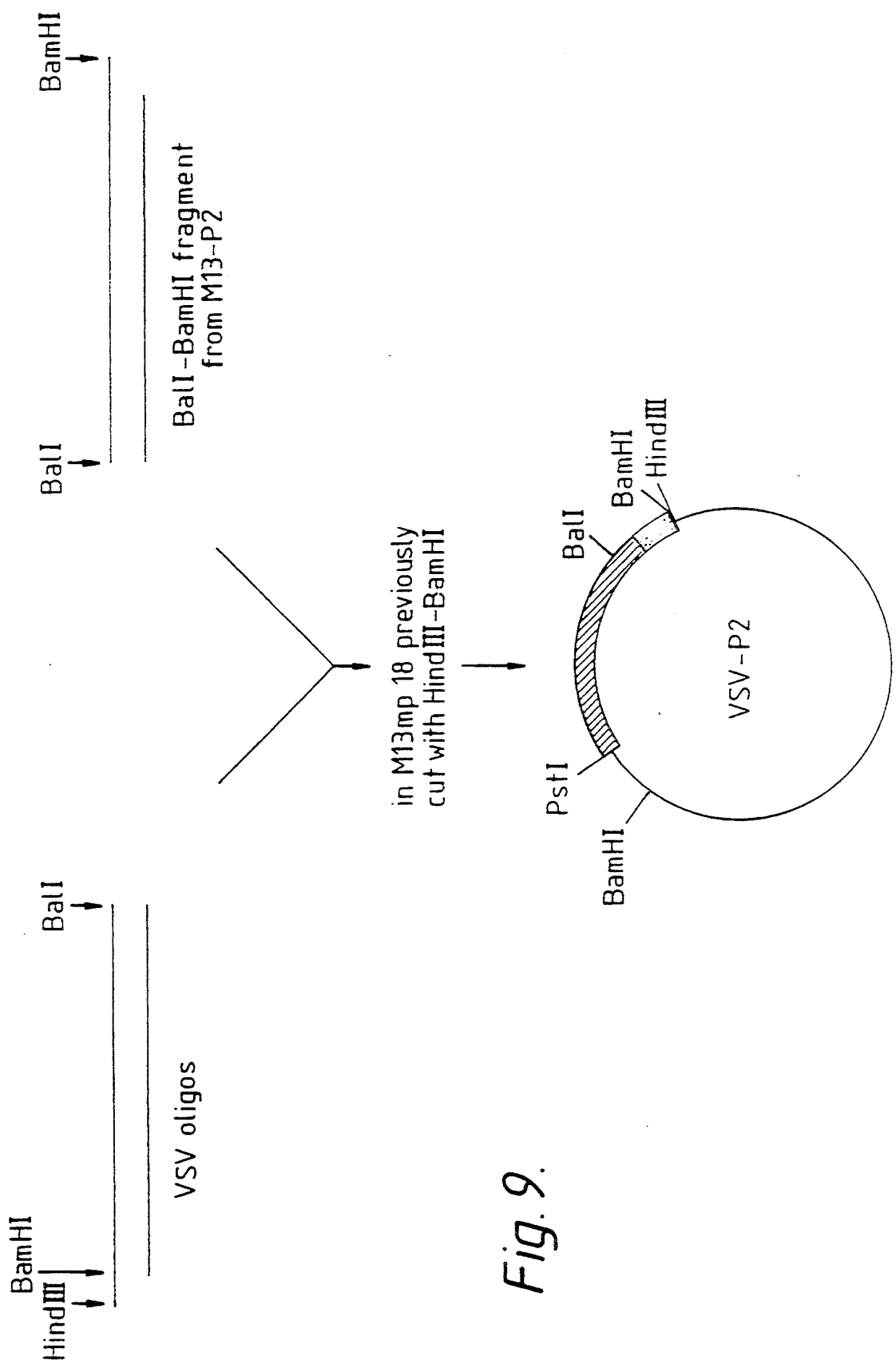
FIG. 9 is a schematic representation of the construction of a new recombinant M13, named VSV-P2, where the complete P2 gene is linked to the VSV G protein leader peptide.
Figure 10:
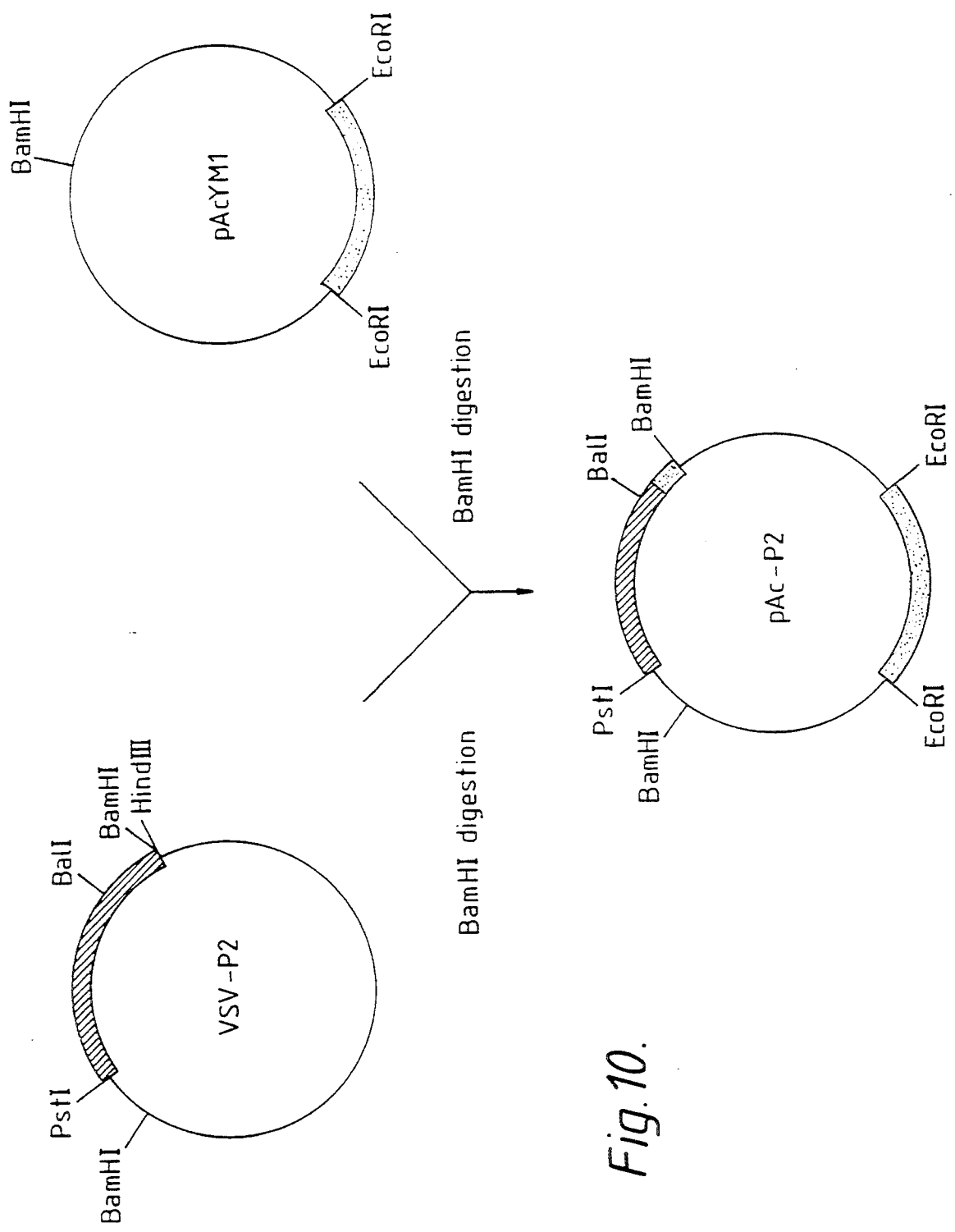
FIG. 10 shows schematically the construction of pAc-P2 which has been used as transfer vector to the baculovirus genome. pAcYM1 is the starting plasmid widely used as acceptor of heterologous sequences to be transferred to the virus.

The synthetic HindIII-BalI fragment was joined to a purified BalI-BamHI fragment from M13-P2 carrying the P2 gene and inserted in M13mp18 previously cut with HindIII and BamHI. This construction which yielded a new plasmid named VSV-P2 is schematically shown in FIG. 9. From VSV-P2 we have excised a BamHI-BamHI DNA fragment carrying the P2 gene fused to the VSV leader peptide which was then inserted into the vector pAcYM1[19], as shown in FIG. 10. The resulting plasmid was named pAc-P2.

To obtain expression in insect cells, the VSV-P2 coding sequence must be transferred to the baculovirus genome under the transcriptional control of the polyhedrin promoter. For this purpose, we co-transfected insect cells with a wild-type baculovirus DNA and with the transfer vector pAc-P2. As insect cells, Spodoptera frugiperda cells were chosen as host cells. Experimental details are as follows:

S. frugiperda cells were transfected with a mixture of infectious AcNPV DNA and plasmid DNA representing the individual recombinant transfer vectors by a modification of the procedure described by Summers et al[20]. One microgram of viral DNA was mixed with 25–100 μg of plasmid DNA and precipitated with (final concentrations) 0.125M calcium chloride in the presence of 20 mM HEPES buffer, pH 7.5, 1 mM disodium hydrogen orthophosphate, 5 mM potassium chloride, 140 mM sodium chloride and 10 mM glucose (total volume 1 ml).

The DNA suspension was inoculated onto a monolayer of $10^6$ S. frugiperda cells in a 35-mm tissue culture dish, allowed to adsorb to the cells for 1 h at room temperature, then replaced with 1 ml of medium. After incubation at 28° C. for 3 days the supernatant fluids were harvested and used to produce plaques in S. frugiperda cell monolayers. Plaques containing recombinant virus were identified by their lack of polyhedra when examined by light microscopy. Virus from such plaques was recovered and after further plaque purification was used to produce polyhedrin-negative virus stocks.

The above procedure allowed us to isolate a recombinant baculovirus whose genome carried the P2 gene under control of the polyhedrin promoter and of the VSV G protein leader peptide. We used this virus to infect S. frugiperda cells according to well-established procedures[20], at a multiplicity of infection of 10. Infected cells were then cultivated in spinner culture or in monolayers in the presence of 10% foetal calf serum according to published methods[20]. In both conditions, the S-2238 chromogenic assay showed the presence of an anti-thrombin activity in the culture supernatants of the infected cells.

Example 6: Expression of protein P2 in the cytoplasm of insect cells

Protein P2 could also be produced and accumulated in the cytoplasm of S. frugiperda cells. This approach generally gives a better yield of heterologous proteins since it utilizes the expression signals of polyhedrin which is a non-secreted viral protein.

Our approach to obtain large quantities of recombinant protein P2 is based on the expression of a fusion polypeptide where the first 18 amino acids of polyhedrin are joined in frame to the 64 amino acids of P2. The presence of the NH2 end sequence of polyhedrin allows high level expression[21]. In addition, between the polyhedrin portion and the P2 sequence we put a methionine residue which allows the release of the P2 moiety by treatment of the hybrid protein with CNBr.

Figure 11:
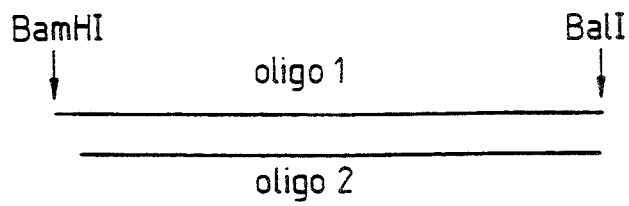
FIG. 11 shows the nucleotide sequence and assembling of the synthetic oligos coding for the beginning of the P2 chain. The ATG codon coding for the additional methionine residue is shown in bold face.

Similarly to the previous approaches, we prepared a synthetic DNA fragment which could allow the joining of the BalI-BamHI fragment from M13-P2 to an appropriate transfer vector. The new synthetic piece, shown in FIG. 11, (SEQ ID NOS: 27–28) includes also BamHI and BalI sites for subsequent manipulations.

Figure 12:
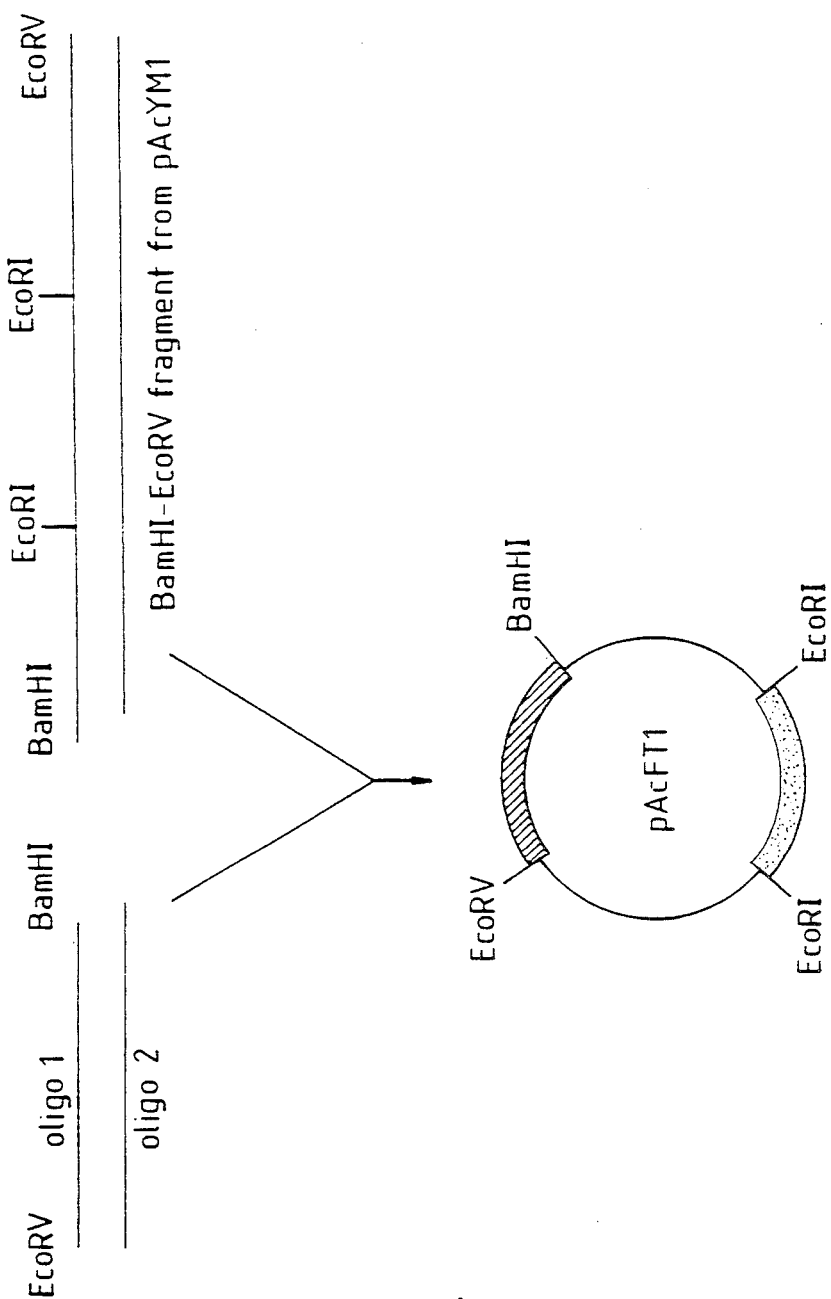
FIG. 12 shows schematically the construction pAcFT1, which has been used for intracellular expression.
Figure 13:
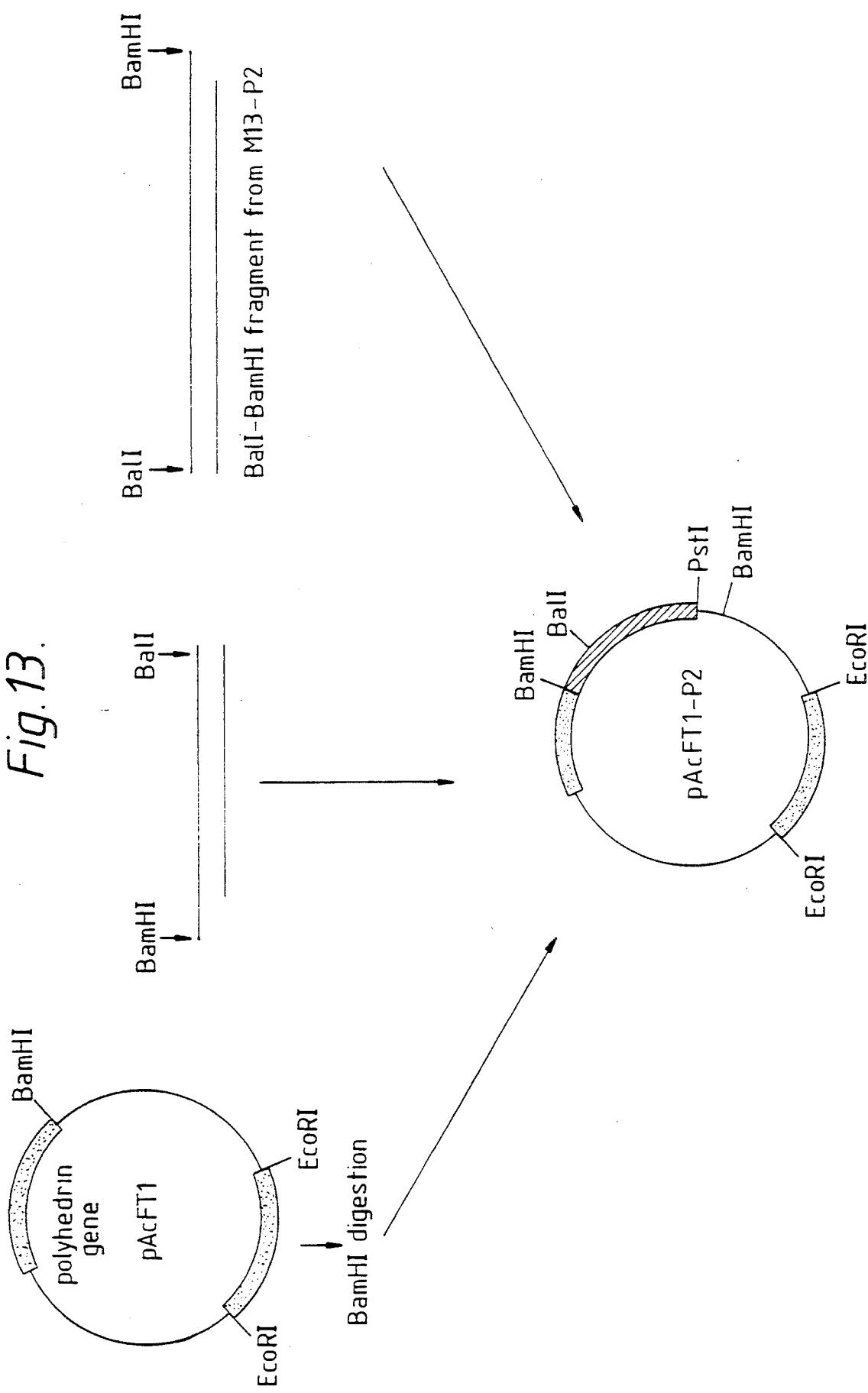
FIG. 13 is a schematic representation of a new transfer plasmid, named pAcFT1-P2, which carries the complete P2 sequence linked to the first 18 amino acids of polyhedrin. This plasmid has been used to transfer the heterologous sequence to the baculovirus genome.

A different transfer vector, pAcFT1, carrying the nucleotide sequence coding for the first 18 amino acids of polyhedrin has been obtained (FIG. 12). Briefly, the EcoRV-BamHI fragment of pAcYM119 has been replaced by a synthetic oligonucleotide containing the polyhedrin gene sequence from nucleotide −92 to nucleotide +55. A convenient BamHI site is present after this sequence and it has been used for insertion of the complete P2 coding sequence according to a scheme illustrated in FIG. 13. Through this construction, we obtained a new plasmid, named pAcFT1-P2, which has been used to transfer the hybrid gene to the baculovirus genome.

The recombinant baculovirus was obtained as described in Example 5. Infection of S. frugiperda cells was carried out according to standard procedures[20]. Cultivation of infected insect cells lead to the cytoplasmic accumulation of the fusion protein. This hybrid protein was the source of recombinant protein P2. Several methods are available from the literature which can be used to cleave the hybrid with CNBr[22,23]. The application of the method of Olson et al[23], has allowed us to obtain the correct polypeptidic sequence of P2. This molecule displayed antithrombin activity.

Example 7

In order to obtain the $Tyr_{61}$ variant of the P2 protein, oligonucleotides number 5 and 6 described above in Example 3 and shown in FIG. 3 have been substituted with the following ones oligo 5-Tyr
5′CGAAATCTCAGACTGAAGGTGACTTCGAAGAAATTCCGGACGAATACATCCTG
AACTAGTAACTGCA 3′ oligo 6-Tyr
5′-GTTACTAGTTCAGGATGTATTCGTCCGGAATTTCTTCGAAGTCACCTTCA 3′

In oligo 5-Tyr the triplet TAC which is underlined codes for a tyrosine residue and substitutes the GAC triplet coding for aspartic acid originally present. Oligo 6-Tyr has been corrected accordingly in order to obtain a complete complementarity between the two strands. The following steps leading to the expression and/or secretion of the variant in insect cells or in E. coli are the same described above in Examples 4 to 6.

Example 8

In order to obtain a glycine-extended derivative of the P2 protein, oligonucleotides 5 and 6 described above in Example 3 and shown in FIG. 3 have been substituted with the following ones:

oligo 5-Gly
5′CGAAATCTCAGACTGAAGGTGACTTCGAAGAAATTCCGGACGAAGACATCCTGAAC—
GGTTAGTAACTGCA 3′ oligo 6-Gly
5′ GTTACTAACCGTTCAGGATGTCTTCGTCCGGAATTTCTTCGAAGTCACCTTCA 3′

In oligo 5-Gly the triplet GGT which is underlined and which codes for glycine has been inserted before the stop codon. Oligo 6-Gly has been corrected accordingly in order to obtain a complete complementarity between the two strands. The following steps leading to the expression and/or secretion of the gly-extended derivative in insect cells or in *E. coli* are the same described above under Examples 4 to 6.

Example 9: cDNA cloning of P1 and P2

(a) Total RNA from *Hirudinaria manillensis'* heads was prepared according to Cathala et al[24].

(b) The reverse transcription reaction was performed as follows:

| | | |
|---|---|---|
| 10 μg | of total RNA from leeches' heads | |
| 1 μg | of dT17 adaptor primer | |
| 8 μl | of 5 mM dNTPs mix | |
| 8 μl | of AMV Buffer 5X | |
| H₂O | to 40 μl | | were assembled on ice, mixed and the mixture was heated for 2 minutes at 65° C. followed by quenching on ice. 10 units of RNAsin (Promega) and 20 units of AMV reverse transcriptase (Boehringer Mannheim) were added, followed by incubation at 42° C. for 2 hours. The reaction mixture was then phenolchloroform extracted and isopropanol precipitated.

c) Polymerase chain reaction (PCR) reactions were then carried out. The general scheme for each PCR reaction is outlined below: PCR mixture:

μl of mineral oil. The reaction was cycled in a Cetus/Perkin-Elmer DNA Thermal Cycler.

The cycle profile was:

| | | |
|---|---|---|
| 3 min. | 94° C. | 1 cycle |
| 2 min. | 60° C. | |
| 2 min. 30 seconds | 72° C. | |
| 1 min. | 94° C. | 30 cycles |
| 2 min. | 60° C. | |
| 3 min. 30 seconds | 72° C. | |
| 1 min. | 94° C. | 1 cycle |
| 2 min. | 60° C. | |
| 5 min. | 72° C. | |
| 7 min. | 72° C. | |
| leave at | 25° C. | |

The residual Taq polymerase was inactivated with phenolchloroform and ethanol precipitation; samples could be stored at −20° C. To obtain the complete sequences of P1 and P2 cDNAs, three rounds of PCR amplification were performed. The sequences of each primer used are shown below. Positions at which a degeneracy was introduced into the oligonucleotide sequence are indicated by the alternative nucleotides shown under the primer sequence (N signifies that all four nucleotides were used). Restriction sites, added to facilitate cloning of the amplification products, are underlined.

```
dT17 adaptor primer:
5' GAC TCG AGT CGA CAT CGA TTT TTT TTT TTT TTT TT 3'

XhoI      SalI

Adaptor primer:
5' GAC TCG AGT CGA CAT CG 3'

XhoI      SalI

Primer 3-8
5' ATC GAA GCT TTA TAC CGA TTG TAC NGA 3'

HindIII       C    A    C    C
                                T

Primer 52-56
5' CTA AGG ATC CTT CTT CGA AGT CNC C 3'

BamHI         C    A    A

Primer 32-37
5' ATC GGA ATT CAG TTC TGG AAA TCA GTG CGT 3'

EcoRI

Primer 5' I
5' CTA AGA ATT CTT CGC AAC TTA TAT GCG TT 3'

EcoRI

Primer 5' II
5' ATC GGA ATT CTT AAT TCA ATA TAT CTT CAT 3'

EcoRI
```

| | |
|---|---|
| 5 μl | of reverse transcribed RNA |
| 10 μl | of 10X PCR Buffer (Cetus/Perkin Elmer) |
| 16 μl | of dNTPsMix (1.25 mM each DNTP) |
| 2 μl | of MgCl2 0.1M |
| 25–500 pmoles | of each primer |
| H₂O | to 100 μl |

The reaction mixture was denatured at 95° C. for 5 minutes prior to the addition of 2.5 units of Taq polymerase (Cetus/Perkin-Elmer) and then overlaid with 80

First round of amplification 500 pmoles of fully degenerated primers, spanning from residue 3 to 8 and from residue 56 to 52 of the P2 amino acid sequence were used as opposing primers in the PCR reaction.

Amplification of cDNA 3' ends (RACE protocol) Frohman et al[25].

Figure 14:
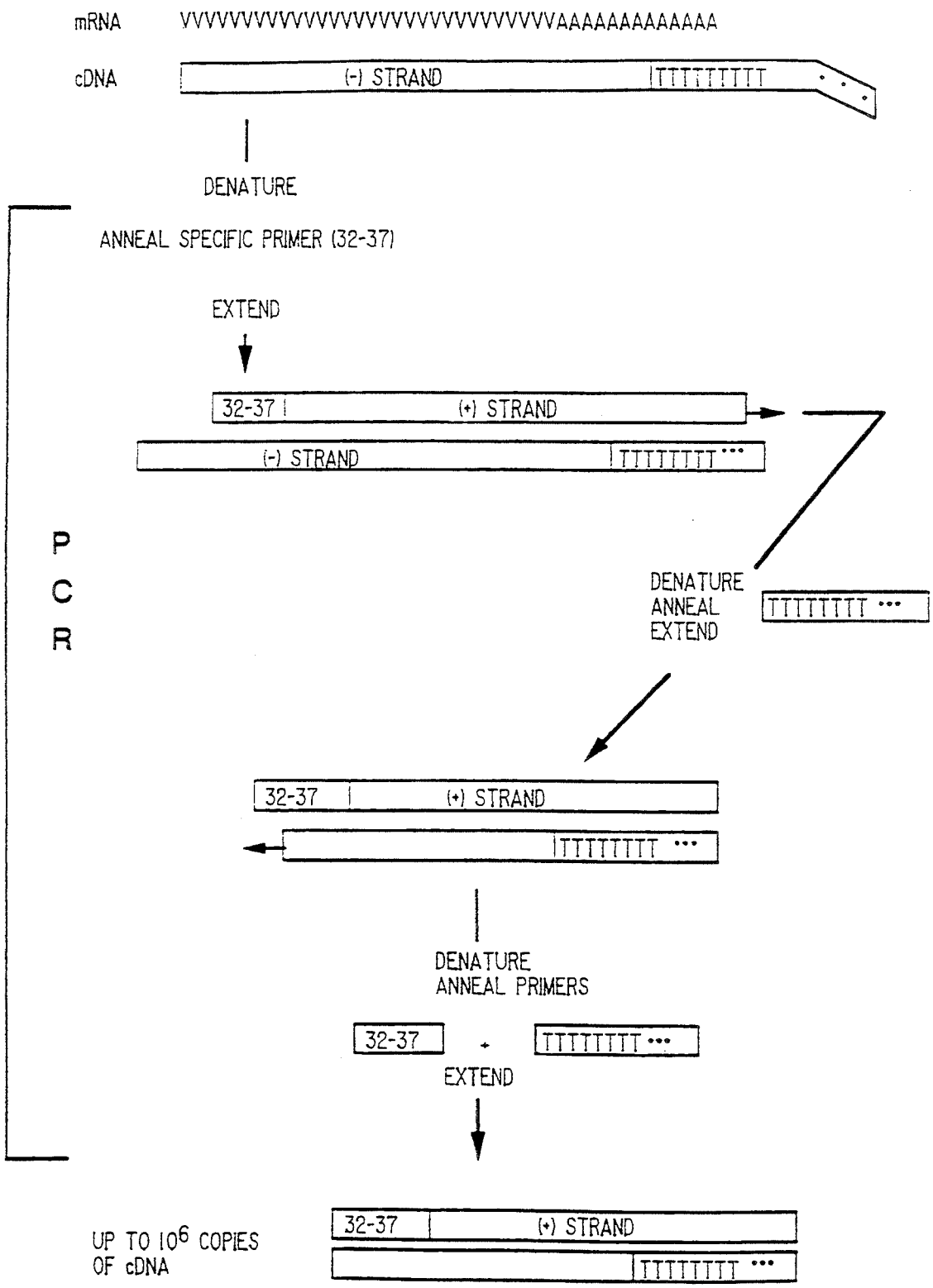
FIG. 14 is a schematic representation of the RACE protocol for amplification of 3' ends. In the Figure "***TTTT..." represents the dT17 adaptor primer. At each step the diagram is simplified to illustrate only how the new product formed during the previous step is utilized.

A gene specific primer, spanning from residue 32 to 37 was designed on the basis of the nucleotide sequence of P2 determined in the first round of amplification. This was used together with the dT adaptor primer to amplify the cDNA (FIG. 14).

Amplification of cDNA 5' ends (RACE protocol), Frohman et al[25].

Figure 15:
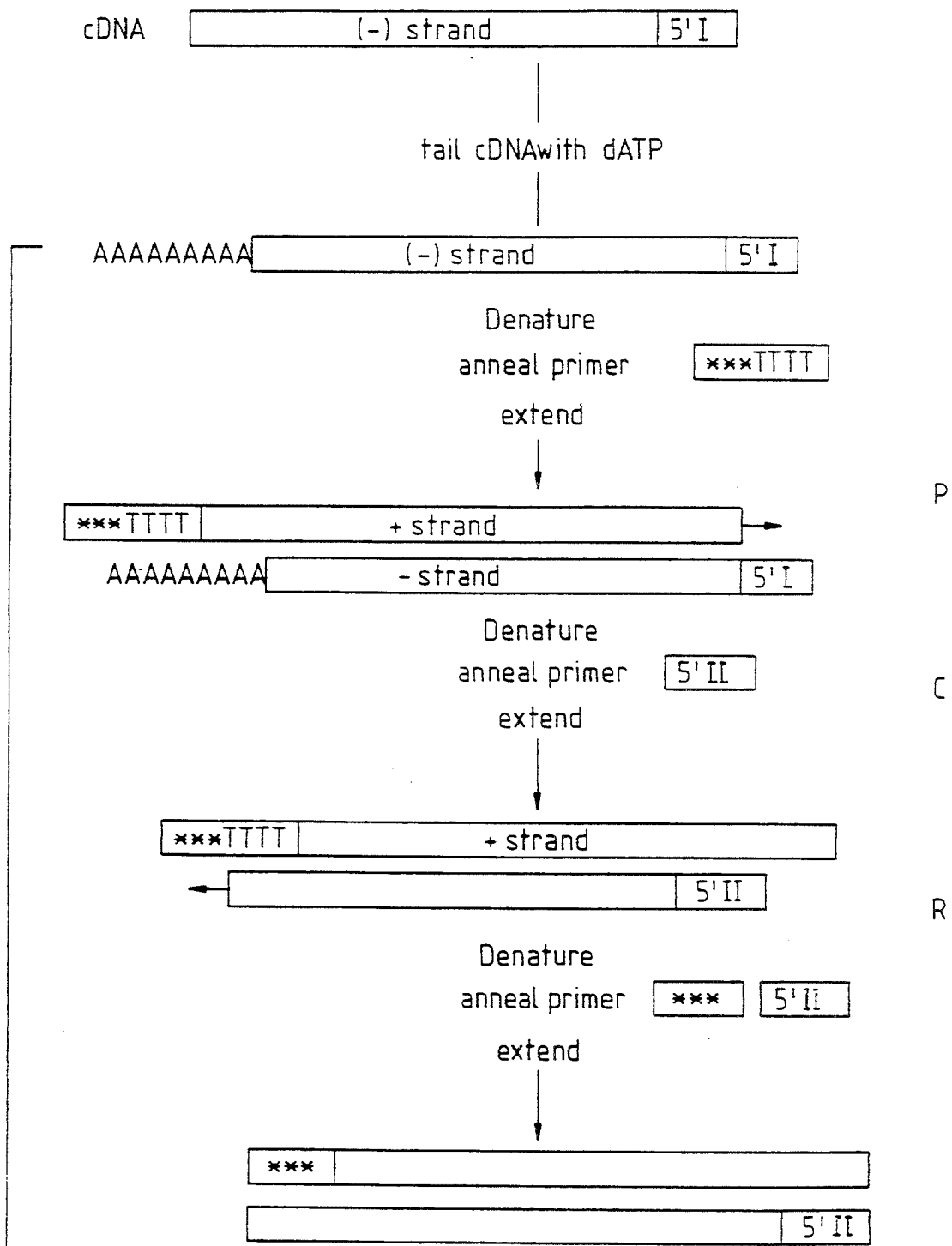
FIG. 15 is a schematic representation of the RACE protocol for amplification of 5' ends. In the Figure "*TTTT..." and "*" respectively represents the dT17 adaptor primer and the adaptor primer. At each step the diagram is simplified to illustrate only how the new product formed during the previous step is utilized.

10 μg of total RNA from leeches' heads were reverse transcribed as previously described except for the substitution of 1 μg of a gene specific primer (5'I) for dT17 adaptor primer (see FIG. 15). The reaction mixture was then isopropanol precipitated and the first strand cDNA products were polyadenylated at their 5' ends using Terminal deoxynucleotidyltransferase (TdT) as follows:

specific primer upstream to the first specific used for transcription (5' II, see FIG. 15).

d) Analysis of PCR products

The amplified products were cleaved at restriction sites present in each primer. The digested product was gel purified and subcloned into pUC13 vector, previously digested with the same restriction enzymes. Plasmids carrying the insert of interest were identified by restriction analyses. Plasmid DNA was sequenced with Sequenase (USB) using the supplier's recommendations. The cDNA sequences of P1 and P2 thus obtained and the deduced amino acid sequences are as follows. Leader sequences are underlined.

P1 cDNA tca aaa ATG TTC TCT CTC AAG TTG TTC GTT GTC TTC CTG GCT GTT
        Met Phe Ser Leu Lys Leu Phe Val Val Phe Leu Ala Val TGC ATC TGC GTG TCT CAA GCA GTG AGC TAC ACT GAT TGT ACG GAA
Cys Ile Cys Val Ser Gln Ala Val Ser Tyr Thr Asp Cys Thr Glu TCA GGC CAG AAT TAT TGT CTA TGC GTG GGA GGT AAT CTC TGC GGT
Ser Gly Gln Asn Tyr Cys Leu Cys Val Gly Gly Asn Leu Cys Gly GGA GGC AAA CAT TGT GAA ATG GAC GGT TCT GGA AAT AAA TGC GTC
Gly Gly Lys His Cys Glu Met Asp Gly Ser Gly Asn Lys Cys Val GAT GGG GAA GGT ACT CCG AAG CCT AAG AGC CAG ACT GAA GGC GAT
Asp Gly Glu Gly Thr Pro Lys Pro Lys Ser Gln Thr Glu Gly Asp TTC GAA GAA ATC CCA GAT GAA GAT ATA TTG AAT TAA
Phe Glu Glu Ile Pro Asp Glu Asp Ile Leu Asn End SEQ ID NO. 47 encodes mature P1, i.e., amino acid 21 (Val) through the stop codon (TAA). SEQ ID NO. 48 encodes amino acids 1 (Met) through the stop codon (TAA) of P1. SEQ ID NO. 49 encodes amino acid 1 (Met) through amino acid 20 (Ala) which is the leader sequence of both P1 and P2.

aaa ATG TTC TCT CTC AAG TTG TTC GTT GTC TTC CTG GCT GTT TGC
    Met Phe Ser Leu Lys Leu Phe Val Val Phe Leu Ala Val Cys ATC TGC GTG TCT CAA GCA GTG AGC TAC ACT GAT TGT ACG GAA TCA
Ile Cys Val Ser Gln Ala Val Ser Tyr Thr Asp Cys Thr Glu Ser GGT CAG AAT TAT TGT CTA TGC GTG GGA AGT AAT GTC TGC GGT GGA
Gly Gln Asn Tyr Cys Leu Cys Val Gly Ser Asn Val Cys Gly Glu GGC AAA AAT TGT CAA CTG AGC AGT TCT GGA AAT CAG TGC GTC CAT
Gly Lys Asn Cys Gln Leu Ser Ser Ser Gly Asn Gln Cys Val His GGG GAA GGT ACT CCG AAG CCT AAG AGC CAG ACT GAA GGC GAT TTC
Gly Glu Gly Thr Pro Lys Pro Lys Ser Gln Thr Glu Gly Asp Phe GAA GAA ATC CCA GAT GAA GAT ATA TTG AAT TTA cgaacgcatataagt
Glu Glu Ile Pro Asp Glu Asp Ile Leu Asn End tgcgaataattctgattttaagacattcccatcgcagctatggctatttacagtatatta
ttataaataaagaattgaacgtttacgttgattgta

| 22 μl of cDNA |
| 1 μl of 6 mM dATP |
| 6 μl of 5X TdT Buffer (BRL) |
| 1.1 μl of TdT (BRL) |

Samples were incubated for 10 minutes at 37° C. and heated for 16 minutes at 65° C. The reaction mixture was then diluted to 500 μl in distilled water.

10 μl of the polyadenylated products were amplified using 10 pmoles of the dT17 adaptor primer, 25 pmoles of the adaptor primer and 25 pmoles of a second gene- References 1) Markwardt, F. 1970, Methods in Enzymology, 19, p. 924
2) Markwardt, F. 1985, Biomed. Biochim. Acta. 44, P. 1007
3) Markwardt, F. Hauptmann, J., Nowak, G., Klessen, C., and Walsmann, P. 1982. Thromb. Haemostasis 47, P. 226.

4) Dupont D., Keim P., Chui A., Bello R. and Wilson K., Derivatizer-Analyser User Bulletin No. 1, Applied Biosystems Inc., 1987
5) Grosjeans H. and Fiers W. 1982. Gene, 18, p. 199
6) Maniatis T., Fritsch E. F. and Sambrook J. 1982. Cold Spring Harbor, N.Y.
7) Sanger, F., Nicklen, S., and Coulson, A. R. 1977, Proc. Natl. Acad. Sci. USA 74, p. 5463.
8) Blobel G. and Dobberstain B. 1975. J. Cell Biology, 67, p. 83
9) Pages J. M. 1983, Biochimie, 65, p. 531
10) Wolfe P. B. 1983. J. Biol. Chem. 258, p. 12073
11) Talmadge K., Stahl S. and Gilbert W. 1980. Proc. Natl. Acad. Sci. USA, 77, p. 3369
12) Oka T., Sakamoto S., Miyoshi K., Fuwa T., Yoda K., Yamasaki M., Tamura G. and Miyake K. 1985. Proc. Natl. Acad. Sci. USA, 82, p. 7212
13) Henning V., Royer H. D., Teather R. M., Hindennach I. and Hollenberg C. P. 1979. Proc. Natl. Acad. Sci. USA, 76, p. 4360
14) Isacchi A., Sarmientos P., Lorenzetti R. and Soria M. 1989, Gene 81, p. 129
15) Mandel M. and Higa A. J. 1970. J. Mol. Biology, 59, p. 154
16) Krstenansky, J. K., and Mao, S. J. T. 1987. FEBS Lett. 211, p. 10
17) Ghrayeb J., Kimura H., Takahara M., Hsiung H., Masui Y. and Inouye M. 1984. EMBO Journal 3, p. 2437
18) Bailey, M. J., McLeod, D. A., Kang, C., and Bishop, D. H. L. 1989. Virology 169, p. 323
19) Matsuura, Y., Possee, R. D., Overton, H. A. and Bishop. D. H. L. 1987. J. Gen. Virol. 68, p. 1233
20) Summers, M. D., and Smith, G. E. 1987, Texas Agricultural Experiment Station Bulletin No. 1555
21) Luckow, V. A. and Summers, M. D. 1988, Virology, 167, p.56
22) Gross E. 1967. Methods in Enzymology, 11, p. 238
23) Olson H., Lind P., Pohl G., Henrichson C., Mutt V., Jornvall H., Josephson S., Uhlen M. and Lake M. 1987, Peptides, 9, p. 301
24) Cathala, G., Savouret, J. F., Mendez, B., West, B. L., Karin, M., Martial, J. A. and Baxter, J. D. (1983) DNA, 2,4: 329–335
25) Frohman, M. A., Dush, M. K. and Martin, G. R. (1988) Proc. Natl. Acad. Sci. USA 85:8998–9002

We claim:

1. An expression vector comprising a DNA sequence encoding a polypeptide having the amino acid sequence of SEQ ID NO: 1, 2, 3, 50, 51, 52, 53, 54, 56, 57, 58 or 59.

2. A vector according to claim 1, which is a plasmid.

3. A vector according to claim 1, which is a virus.

4. A vector according to claim 3, wherein the virus is a recombinant baculovirus in which the polyhedrin promoter is operably linked to the said DNA sequence.

5. A vector according to claim 1, wherein the said DNA sequence further encodes a leader peptide capable of directing secretion of the said polypeptide from cells in which the said polypeptide is expressed.

6. A vector according to claim 1, wherein the said DNA sequence encodes a fusion protein which is cleavable to release the polypeptide.

7. A host cell transformed with a compatible expression vector according to claim 1.

8. A host according to claim 7, which is a bacterium, yeast, mammalian cell line or insect cell line or animal.

9. A host according to claim 8, which is a strain of *E. coli* type B or a *Spodoptera frugiperda* cell line.

10. A DNA sequence encoding a polypeptide having the amino acid sequence of SEQ ID NO: 1, 2, 3, 5.0, 51, 52, 53, 54, 56, 57, 58 or 59.

11. A DNA sequence according to claim 10, which is a synthetic DNA sequence.

12. A DNA sequence according to claim 10, which is a cDNA.

13. A DNA sequence according to claim 10, which further encodes a leader peptide capable of directing secretion of the said polypeptide from cells in which the said polypeptide is expressed.

14. A DNA sequence according to claim 10, which encodes a fusion protein which is cleavable to release the said polypeptide.

15. The DNA sequence according to claim 10, which consists of:

GTTTCTTACACCGACTGCACCGAATCTGGCCAGAACTACTGCCTGTGCGTTGGTTCTAAC

GTTTGCGGTGAAGGTAAAAACTGCCAGCTGTCTTCTTCTGGTAACCAGTGCGTTCACGGT

GAAGGTACCCCGAAACCGAAATCTCAGACTGAAGGTGACTTCGAAGAAATTCCGGACGAA

GACATCCTGAACTAG.

16. The DNA sequence according to claim 10, which consists of:

GTG AGC TAC ACT GAT TGT ACG GAA TCA GGC CAG AAT TAT TGT CTA

TGC GTG GGA GGT AAT CTC TGC GGT GGA GGC AAA CAT TGT GAA ATG

GAC GGT TCT GGA AAT AAA TGC GTC GAT GGG GAA GGT ACT CCG AAG

CCT AAG AGC CAG ACT GAA GGC GAT TTC GAA GAA ATC CCA GAT GAA

GAT ATA TTG AAT TAA.

17. The sequence according to claim 10, which consists of:

ATG TTC TCT CTC AAG TTG TTC GTT GTC TTC CTG GCT GTT TGC ATC

TGC GTG TCT CAA GCA GTG AGC TAC ACT GAT TGT ACG GAA TCA GGT

CAG AAT TAT TGT CTA TGC GTG GGA AGT AAT GTC TGC GGT GGA GGC

AAA AAT TGT CAA CTG AGC AGT TCT GGA AAT CAG TGC GTC CAT GGG

GAA GGT ACT CCG AAG CCT AAG AGC CAG ACT GAA GGC GAT TTC GAA

GAA ATC CCA GAT GAA GAT ATA TTG AAT TAA.

18. A DNA sequence according to claim 16, wherein the depicted sequence is immediately preceded by the sequence:

ATG TTC TCT CTC AAG TTG TTC GTT GTC TTC CTG GCT GTT TGC ATC
TGC GTG TCT CAA GCA.

\* \* \* \* \*